United States Patent [19]

Wagner

[11] 4,322,523
[45] Mar. 30, 1982

[54] METHYLOLATED MONO- AND OLIGOSACCHARIDES

[75] Inventor: Kuno Wagner, Leverkusen, Fed. Rep. of Germany

[73] Assignee: Bayer Aktiengesellschaft, Leverkusen, Fed. Rep. of Germany

[21] Appl. No.: 60,241

[22] Filed: Jul. 25, 1979

[30] Foreign Application Priority Data

Jul. 28, 1978 [DE] Fed. Rep. of Germany ....... 2833138

[51] Int. Cl.³ .................. C07H 15/04; C07H 1/00
[52] U.S. Cl. .................. 536/4; 521/155; 521/158; 521/107; 521/109; 536/1; 536/2; 536/18; 536/95; 536/102; 536/115; 536/117; 536/120; 560/157; 528/272; 528/405; 536/43; 536/30
[58] Field of Search .............. 536/1, 4, 120, 2, 43, 536/18, 30, 95, 102

[56] References Cited

U.S. PATENT DOCUMENTS

| | | |
|---|---|---|
| 1,018,736 | 2/1912 | Alsleben .................. 536/1 |
| 2,730,505 | 1/1956 | Jordan .................. 536/114 |
| 3,202,620 | 8/1965 | Merlen et al. .................. 536/1 |
| 3,455,895 | 7/1969 | Niilo-Rama et al. .................. 536/1 |
| 3,839,173 | 10/1974 | Blaszczak .................. 536/1 |
| 4,056,672 | 11/1977 | Aktiebolag .................. 536/1 |
| 4,247,654 | 1/1981 | Wagner .................. 521/158 |

FOREIGN PATENT DOCUMENTS

1088558 10/1980 Canada .................. 536/04

OTHER PUBLICATIONS

HO, "Tetrahedron Letters", No. 19, 1978, pp. 1623-1626.
Depezay et al., "Tetrahedron Letter", No. 32, 1978, pp. 2865-2868, 2869-2872.
Langenbeck "Lehrbuch DerOrganischen Chemie", Dresden Und Leipzig, 1948, Verlag Von Theodor Steinkopff, pp. 258-264.
Shallenberger et al., *Sugar Chemistry*, p. 47, (Westport, Connecticut, 1975).
Schaffer, "Occurrence, Properties and Preparation of Naturally Occurring Monosaccharides (Including 6-Deoxy Sugars)", from Pigman et al. (eds. *The Carbohydrates: Chemistry and Biochemistry*), pp. 69-93 (New York, 1972).
CRC Handbook, pp. C745-C752.

Primary Examiner—Johnnie R. Brown
Attorney, Agent, or Firm—Gene Harsh; Joseph C. Gil; Lyndanne M. Whalen

[57] ABSTRACT

This invention is directed to a derivative of a reducing sugar, said reducing sugar having molecular weights of from 120 to 2000, in that said derivative having at least one methylol group which branches the carbon structure of the reducing sugar in the α- and/or α'-position to the carbonyl group or cyclohemiacetal group of the reducing sugar.

46 Claims, 1 Drawing Figure

METHYLOLATED MONO- AND OLIGOSACCHARIDES

BACKGROUND OF THE INVENTION

This invention relates to novel derivatives of reducing sugars having molecular weights of up to 2000 which reducing sugars are C-methylolated in the α- and/or α'-position to the carbonyl group or to a carbonyl group which is masked by cyclohemiacetal formation. By reducing sugars are meant in the context of this invention carbohydrates which reduce Fehling's solution. Such carbohydrates include both natural sugars and derivatives of natural sugars. Specific families of useful carbohydrates include amino sugars, monosaccharides, disaccharides, trisaccharides and oligomeric polysaccharides obtained by partial acid or enzymatic hydrolysis of natural polysaccharides, e.g. of starch (i.e. amylose and amylopectin), cellulose, inulin, hemicelluloses, glycogens and those derived from wood (i.e. cellulose containing lignin). The invention also relates to a new and simple process for the preparation of these α-methylolated derivatives and to their use for various purposes in which their enhanced hydroxyl functionality is of particular interest.

It is known that various carbohydrates which carry cyclohemiacetal end groups and which reduce Fehling's solution (including monosaccharides such as grape sugar (i.e. α- and β-glucose), fructose; disaccharides such as maltose, lactose, cellobiose, and the like; and tri- and oligosaccharides) are subject to rearrangement and decomposition reactions in the presence of alkalies or organic bases (see Langenbeck, Lehrbuch der Org. Chemie (1952), page 258 et seq). The nature and extent of these rearrangement, carmelization, dehydration and polymerization reactions, preliminary stages of carbonization reactions and Cannizzaro reactions between aldose and ketose sugars which take place in a basic medium, often accompanied by pronounced deepening of color, are generally unknown because the reaction and decomposition products are extremely difficult to isolate and are soluble only in water. Accordingly, the possibility of using spectroscopic methods which would identify such products is severely limited or may even be precluded.

Applicants have found that in aqueous solutions the carbohydrates noted above react with formaldehyde, generally at pH values above 7, to yield sugar hemiacetals corresponding to the following schematic structure, which vary from pentafunctional to octafunctional according to the quantity of formaldehyde present:

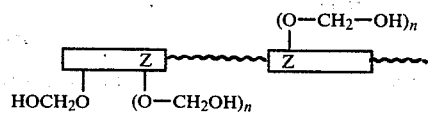

wherein Z means the carbon skeleton of a sugar molecule and n means the number of methylolated hydroxy groups.

In aqueous solution, these sugar hemiacetals are in equilibrium with methylene glycol (HO—CH$_2$—OH). By removal of water at reduced pressure (e.g. from 0.06 to 15 Torr), the pure sugar polyhemiacetals can be obtained. These hemiacetals will, however, readily split off formaldehyde even by hydrolysis in a neutral medium or by heating. Cyclic and chain lengthening or chain branching or cross-linking acetal groups, which are stable to heat and to alkaline hydrolysis, can be introduced into the sugars by dehydration at pH below 5.5 which is accompanied by the elimination of water from the sugar molecules, but these acetal groups are readily split off by hydrolysis at acid pH.

DESCRIPTION OF THE INVENTION

Figure 1:
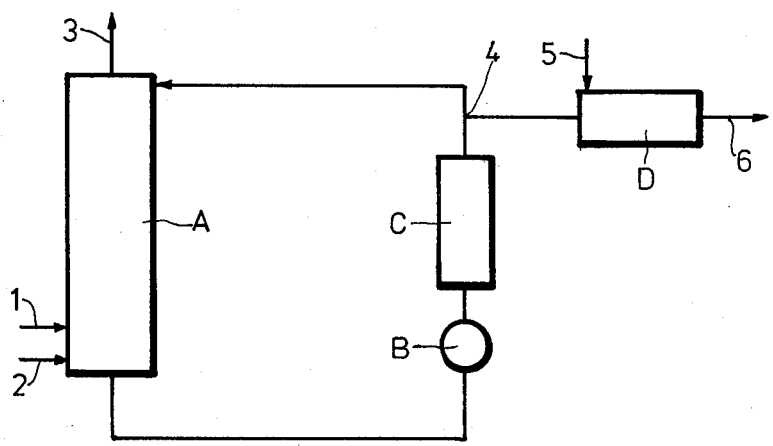
FIG. 1 represents a schematic illustration of an apparatus suitable for performing the process of the invention on a continuous basis.

It has now surprisingly been found that reducing sugars such as natural, optically active sugars and their derivatives, such as α- and β-D-glucose, fructose, aminoglucose, invert sugar, maltose, lactose, cellobiose, trisaccharides and higher molecular oligosaccharides, can be methylolated on their α-C-atoms in the α-position to the carbonyl group without any dehydration, isomerization or other reactions which cause a deep color change. The process is preferably carried out in the presence of catalytic quantities of basic compounds of various kinds at a pH in the range of from 7.4 to 11, preferably from 8 to 9 and most preferably at pH=8.4–8.6. New carbon-to-carbon bonds which are extremely stable to heat and hydrolysis are thereby introduced into the sugars. In the case of aldoses, the primary hydroxyl group functionality is thereby advantageously increased by one unit and in ketoses the number of primary hydroxyl groups can be increased by two or even three, depending on the position of the keto group.

This invention thus relates to derivatives of reducing sugars, said sugars having molecular weights of from 120 to 2000, preferably from 150 to 750, most preferably from 180 to 340 characterized in that they contain at least one methylol group which branches the carbon structure of the sugar in the α- and/or α'-position to the carbonyl group or cyclohemiacetal group of the sugar.

As noted above, the term "reducing sugar" is defined herein as a carbohydrate which reduces Fehling's solution. As mentioned above, useful carbohydrates include not only naturally occurring mono-, di- and oligosaccharides but also to hydrolysates of naturally occurring di- and polysaccharides, provided these hydrolysates reduce Fehling's solution.

The invention also relates to a process for the preparation of the new reducing sugar derivatives, which process is characterized in that a reducing sugar which has a molecular weight of from 120 to 2000, preferably from 150 to 750, most preferably from 180 to 342 is reacted with from 0.05 to 10 mol, preferably from 0.2 to 5 mol, most preferably from 1.0 to 1.5 mol and especially from 1.18 to 1.20 mol of formaldehyde, based on the equivalent number of hydrogen atoms in the α- and α'-position to the carbonyl group or cyclohemiacetal group of the reducing sugar, at a temperature of from 40° to 110° C., preferably from 55° to 90° C., most preferably from 80° to 85° C., and at a pH of from 7.4 to 11, preferably from 8 to 9, optionally in the presence of water and/or monohydric or polyhydric alcohols having molecular weights of from 32 to 150. The reaction is preferably carried out in the presence of from 0.01 to 0.34 equivalents, most preferably from 0.04 to 0.06 equivalents of a preferably organic base, said equivalents being based on the number of hydrogen atoms in the α- and α'-position. The reaction is also preferably conducted in the absence of metal ions, and particularly in the absence of polyvalent metal ions and more particularly in the absence of divalent metal ions. The reaction is stopped by acidification and/or cooling, preferably when the residual formaldehyde content in the reaction mixture is from 0.3 to 0.9% by weight.

The process according to the invention provides a new class of interesting reducing sugar derivatives with clearly defined branching. The process makes it possible to modify a wide variety of carbohydrates such as sugars, aldoses and ketoses and their D,L-racemates. For example, the invention makes it possible for a $CH_2OH$ group to be introduced into the following aldoses at the α-C-atoms indicated by arrows:

I. Group of hexoses:

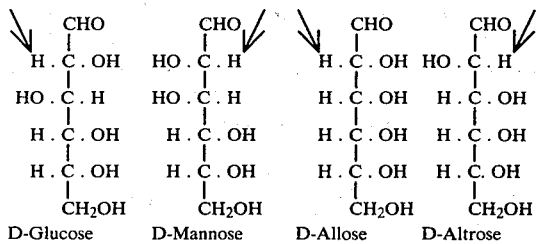

D-Glucose    D-Mannose    D-Allose    D-Altrose

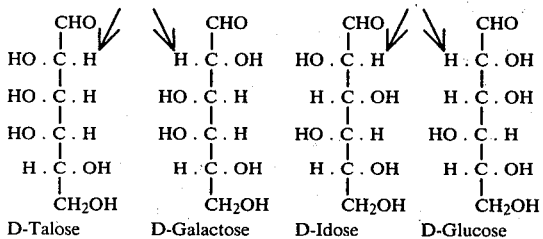

D-Talose    D-Galactose    D-Idose    D-Glucose

II. Group of pentoses:

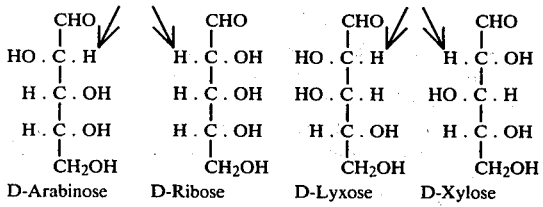

D-Arabinose    D-Ribose    D-Lyxose    D-Xylose

III. Group of tetroses:

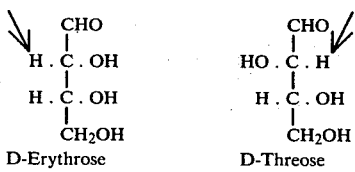

D-Erythrose    D-Threose

The additional primary hydroxyl group introduced according to the invention into the molecule has substantially the same reactivity as that already present and is available for various modification reactions, which will be described in more detail below.

It is probable that in the reducing sugars modified according to the invention, ring closure from the open chain to the cyclohemiacetal form takes place, as illustrated in the following formulae in the case of α-C-methylolated α-D-glucose and β-D-glucose:

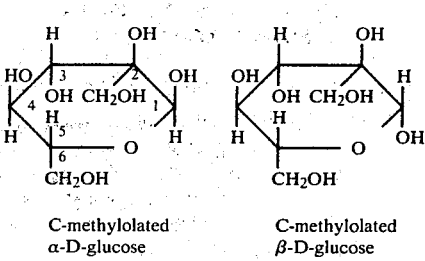

C-methylolated    C-methylolated
α-D-glucose       β-D-glucose

New branched disaccharides with two equivalently reacting primary hydroxyl groups are similarly obtained from reducing disaccharides after α-C-methylolation. In oligosaccharides which have glycocidically bound sugar residues, e.g. in hydrolysates of corn starch, potato starch or grain starch, or in other enzymatically hydrolyzed polysaccharides, α-C-methylolation always increases the number of $CH_2OH$ groups by 1.

In the case of ketoses, up to three methylol groups can be introduced by the process according to the invention since both the α and the α'-carbon atoms in ketoses are sufficiently activated for the addition of formaldehyde, as illustrated below in the examples of D-fructose and D-sorbose:

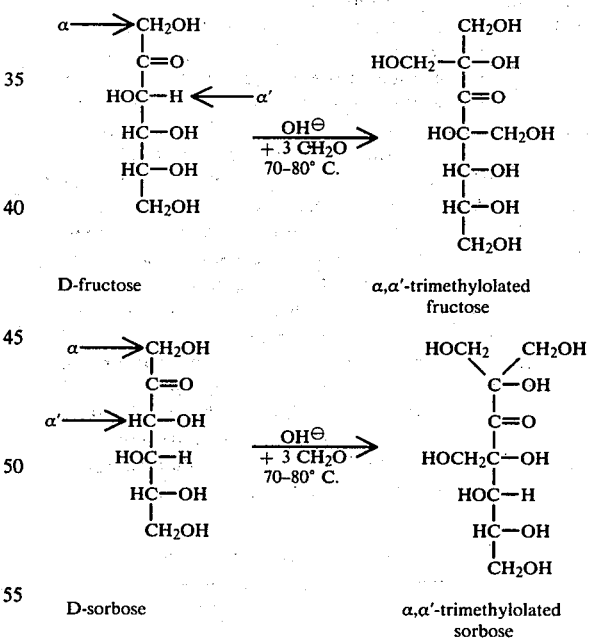

It is particularly advantageous that the introduction of at least one methylol group by the process according to the invention liquefies carbohydrates which are normally crystalline.

The new addition reaction which proceeds with surprising ease and with high yields (94 to 96%) is unexpected in the art since it has hitherto been known that cyclohemiacetals of naturally occurring sugars, e.g. of glucose and fructose:

Cyclohemiacetal of Glucose

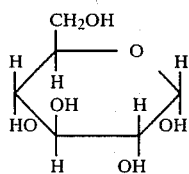

Cyclohemiacetal of Fructose

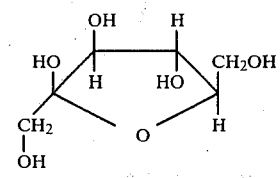

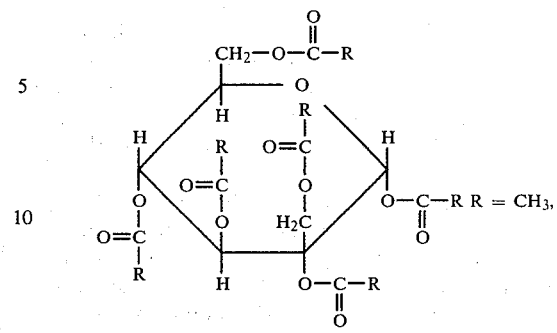

are very stable at basic pH values, in contrast to the acid pH range, which is unsuitable for the process of the invention. It was therefore to be assumed that the cyclohemiacetal structures indicated above would not react due to the insufficient activation of the α- and α′-C-atoms for an addition reaction with formaldehyde to undergo aldol condensation.

It was surprisingly found that the very small quantity of open chain structure present in equilibrium in reducing sugars was nevertheless sufficient to allow the methylolation reaction to take place. In the case of D-glucose and its optically inactive racemates, the course of the reaction may be represented by the following reaction scheme:

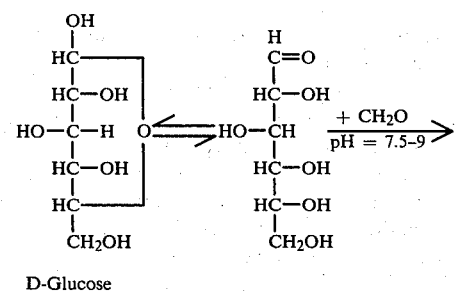

D-Glucose

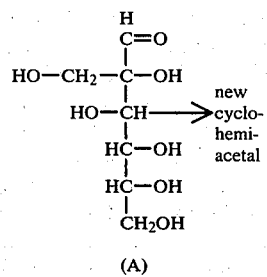

(A)

It is not yet known to what extent the addition reaction according to the invention also gives rise to the optical antipode, i.e. to the L-form of (A). Solutions of (A) are optically active in water and have a rotation of $[\alpha_D] = +31°$. The formation of the new α-C-methylolated branched $C_7$-sugar (A) from glucose and formaldehyde in 95% yield or the formation of the cyclohemiacetal was confirmed by preparing the chloroform-soluble hexacetyl derivative corresponding to the following formula:

by molecular weight determination and by its response to heat.

Another proof of the α-branching of the reducing sugars treated according to the invention is that the usual osazone formation of sugars (binding of 2 mols of phenyl hydrazine) does not occur. The modified sugars according to the invention can bind only 1 mol of phenyl hydrazine, with formation of the hydrazone.

As mentioned above, the methylolation reaction according to the invention is only possible with those carbohydrates and derivatives which reduce Fehling's solution.

In laevoglucosan, a glucose anhydride prepared by the distillation of glucose in accordance with the following equation:

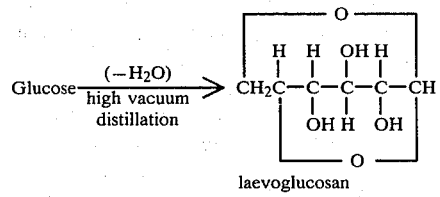

laevoglucosan it is therefore necessary to split the acetal ring before the reaction according to the invention can be carried out.

Sucrose, which is economically the most important disaccharide, i.e. cane sugar or beet sugar, represented by the following formula:

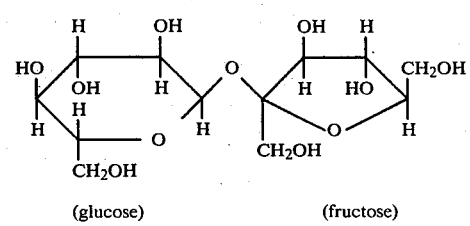

(glucose)          (fructose)

cannot be directly α-C-methylolated in the pH range according to the invention and with the catalysts according to the invention. If, however, the sucrose is converted into invert sugar by acid or ensymatic hydrolysis in known manner (enzymatic decomposition with saccharases or invertases or, for example, H⊕-catalyzed heterogeneous hydrolysis on acid ion exchange resins), one new methylol group can be formed per glucose unit and a maximum of three new methylol groups per fructose unit so that overall, 4 mols of formaldehyde can be introduced as methylol groups according to the invention per mol of sucrose.

Once the capacity of aldoses to be α-methylolated and of ketoses to be α,α'-methylolated was recognized, it became clear that the process of the present invention would be applicable to essentially any monomeric and polymeric sugar, to any D- or L-forms and to their racemate mixtures.

Other valuable starting substances from the family of naturally occurring high molecular weight polysaccharides which do not normally reduce Fehling's solution but are capable of being C-methylolated according to the invention after acid hydrolysis to mono- and oligosaccharides and adjustment of the pH, preferably to 8–9, include: glycoproteids; saponins; inulin $(C_6H_{10}O_5)_x$ (which occurs mainly in the tubers of dahlias, artichokes, Jerusalem artichokes, and the like and is a high polymer polysaccharide of fructose); various pectins (polygalacturonic acids); naturally occurring substances such as tannins; chitin in the form of poly-N-acetylglycosamine; substances which contain nucleotides, such as high molecular ribonucleic acids and deoxyribonucleic acids which contain ribose and deoxyribose ($C_5$-sugars) respectively as chain lengthening element in the main chain; highly branched starches such as glycogen; amylopectins; polymers of D-glucosamine-N-sulphuric acids and D-glucuronic acid (heparin); and chondroitin sulphuric acid which, linked to proteins, is the main constituent of cartilage and consists of D-glucuronic acid, N-acetyl-D-galactosamine and sulphuric acid bound in ester form. Various biologically occurring glycosides, i.e. condensation products of mono- and polysaccharides with alcohols or phenols, are also useful starting materials which may first be hydrolyzed and then α- and α'-C-methylolated. Specific examples of such biologically occurring materials include glycosides of the flavone series which occur in the blue and red pigments of flowering plants and berries; the class of so-called digitalis glucosides; the sugar-containing structural components of tans from the tannin group; mucoitin sulphuric acid which is similar in its molecular structure to chondroitin sulphuric acid but contains N-acetyl-D-glucosamine in place of N-acetyl-D-galactosamine; and high molecular hyaluronic acid which is built up of alternating segments of condensed D-glucuronic acid and N-acetyl-D-glucosamine in a molar ratio of 1:1.

The process of α-C- and α,α'-C-methylolation according to the invention may also be carried out on reducing sugars which have different functional groups, e.g. sugars containing carboxyl groups, such as D-glucoronic acid:

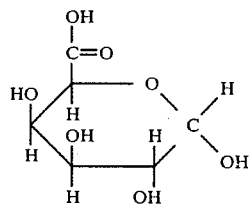

and their esters and alkali metal and ammonium salts; N-acetylglucosamine:

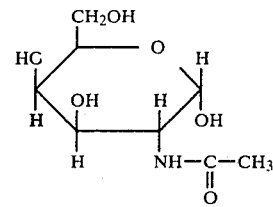

and oligomers of N-acetylglucosamine.

Other saccharide derivatives useful in the present invention include the sodium salts of glucopyranose-6-phosphoric acid ester and fructo-furanose-6-phosphoric acid ester; partially acetalized or ketalized (statistically in the 4, 5 or 6 position) hexoses or pentoses; and partially methylated or acetylated tetroses, pentoses or hexoses and their stereoisomers, provided that these sugar derivatives still contain the hydrogen atoms α to the carbonyl group.

It has also been found that very high molecular polysaccharides such as cellulose, corn starch, potato starch, grain starch, amylopectin, inulin, chitin, choncroitin sulphuric acid, ribonucleic acid and deoxyribonucleic acid, and also the most important disaccharides such as cane and beet sugar and storage polysaccharides occurring in plants; hemicelluloses; and glycogen, which do not reduce Fehling's solution can easily be made useful in the α- and α,α'-addition reactions of formaldehyde according to the invention to form branched sugars by a one pot process. In a first stage of the process these non-reducing sugars are broken down by acid or enzymatic hydrolysis (fermentation) into oligosaccharides having an average molecular weight of from 120 to 2000 so that saccharides and oligosaccharides which reduce Fehling's solution are obtained. After neutralization and, if necessary, removal of the anions on ion exchange columns and removal of any other substances containing nucleotides, such as degraded and hydrolyzed proteins, the resulting sugar mixtures, which will reduce Fehling's solution and which may still contain amino acids and soluble oligopeptides in solution, can be α- or α,α'-C-methylolated according to the invention in a second stage, using formaldehyde or synthesis gases containing formaldehyde.

Hydrolysis of the oligo and polysaccharides may be carried out by one of the known processes of "saccharification of wood" of Bergius or Willstätter and Zechmeister at low temperatures (e.g. with highly concentrated hydrochloric acid) or at elevated temperatures (e.g. using dilute sulphuric acid at normal or elevated pressure and at 100° to 110° C.) by the Scholler-Tornesch process (see Langenbeck, Lehrbuch der Org. Chemie 11/12th Edition, page 291). The same methods may be used for the hydrolytic degradation of bakers' yeast or for the fermentation of various types of yeast used for fermentation, such as high protein nutrient yeast, in order to liberate the sugar-containing nucleotides present and to hydrolyze ribonucleic and deoxyribonucleic acids to riboses and deoxyriboses.

It was particularly interesting to find that cyanohydrins, i.e. products of addition of hydrocyanic acid and aldoses and ketoses as represented by the following idealized formula:

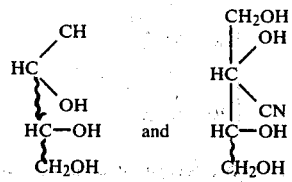

were also useful in the present invention, which resulted in partial slitting off of the hydrocyanic acid with formation of glycol nitrile HO—CH₂CN from formaldehyde and hydrocyanic acid.

It is also of interest and unexpected that the branched $C_7$–$C_9$ sugars obtained from glucose and fructose could be completely fermented with the usual yeast preparations and the speed of ethanol formation represented by the following basic equation of fermentation

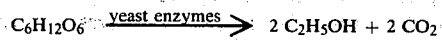

was only slightly reduced.

The following are particularly preferred reducing sugars for use in the process according to the invention: Naturally occurring products such as α- and β-D-glucose (dextrose); acid hydrolyzed or enzymatically hydrolyzed cane sugar (invert sugar) mainly consisting of 1 mol of glucose and 1 mol of fructose: disaccharides such as maltose, lactose and cellobiose; ordinary commercial hydrolyzed or enzymatically degraded corn starch and potato starch in the form of so-called isosyrups; naturally occurring invert sugars such as found in honey; acid hydrolyzed cellulose; products of hydrolysis of inulin which are particularly rich in fructose; naturally occurring sugars which have undergone an Amadori rearrangement, Heyns rearrangement or Lobry de Bruyn rearrangement or Maillard reactions with suitable amines (see Advances in Protein Chemistry, Volume 29, 1975, pages 185–188, Academic Press); hydrolytically degraded oligopolysaccharides containing lignin and glucose-containing sugars obtained from the saccharification of sugar, in which the lignin is present as a polymer of coniferyl alcohol:

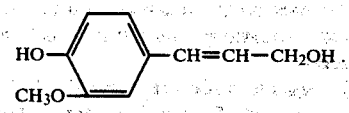

Since the polymer contains approximately one equivalent of aliphatic hydroxyl groups and 0.3 equivalents of aromatic hydroxyl groups per $C_{10}$ monomer unit, hydrolysates of this type, when used in the process according to the invention, give rise to mixtures of α-C-methylolated glucoses according to the invention and hermiacetals of lignin which are C-methylolated in the ortho-position to the phenolic hydroxyl groups. New, modified lignins are thereby obtained in the form of crumbly, amorphous thermoplastic masses with a reddish brown tinge which are characterized by their increased capacity to swell in water and in ethanol.

The process according to the invention may, if desired, also be carried out simultaneously with the abovementioned Amadori, Heyns or Lubry de Bruyn rearrangements or coupled with Maillard reactions to form interesting mixtures of various branched sugar derivatives.

The following are examples of basic catalysts which may be used for the uniform introduction of formaldehyde according to the invention in the α-position or α'-position of reducing sugars:

Hydroxides of lithium, sodium and potassium; sodium, potassium and lithium carbonate; sodium and potassium borate; lithium, sodium and potassium cyanide; potassium acetate; sodium and potassium phenolate; lithium, sodium and potassium salts of peralkylated amino acids, preferably of dimethylaminoglycine:

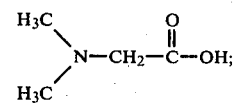

crown ether complexes of alkali metal atoms; sodium, potassium and lithium salts of Mannich bases which contain phenolic hydroxyl groups, e.g. corresponding to the following formula:

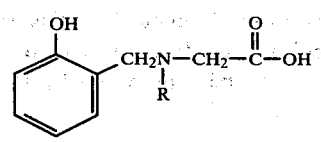

in which R preferably represents a straight or branched chain aliphatic group having from 1 to 8 carbon atoms; and alkali metal salts of tris-2,4,6-dimethylaminophenol.

For the purpose of the invention, it is also possible to use organic bases such as trimethylamine, triethylamine, tri-n-propylamine, tri-n-butylamine, N,N-dialkylbenzylamines having from 1 to 5, preferably 1 or 2, carbon atoms in the alkyl groups; N,N-dimethylcyclohexylamine, N,N-diethylcyclohexylamine, N-alkylpiperidines, N,N'-di-alkylpiperazines and N-alkylmorpholines having from 1 to 5, preferably 1 or 2 carbon atoms in the alkyl groups; N-phenylmorpholine, N-benzylmorpholine, 1,2-bis-morpholylethane and products of addition of ethylene oxide and/or propylene oxide to morpholine or piperazine having molecular weights of up to about 2000, preferably up to about 1000. The last mentioned compounds as well as other basic polyethers known for the production of polyurethanes (alkoxylation products of ammonia and primary and secondary monoamines or polyamines) are interesting for the purpose of the invention because they may be left in the products of the process even at relatively high concentrations. Subsequently, when the products are used as starting components for the production of polyurethanes, they constitute catalysts which can be chemically fixed in the polyisocyanate polyaddition reaction.

Of course, a cross-linked insoluble resin, for example a crosslinked polystyrene, bearing tertiary amino groups may also be mentioned as an organic basic catalyst according to the invention.

Other useful catalysts include bicyclic amidines such as the compounds corresponding to the following formula:

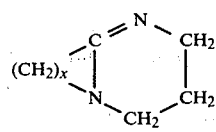

in which x represents 3, 4 or 5; endoethylenepiperazine, permethylated hexamethylenediamine, $N^1,N^2,N^3$-trimethyl- and triethyl-hexahydrotriazine, permethylated alkylene polyamines, N-formylated polyamines such as the compound corresponding to the following formula:

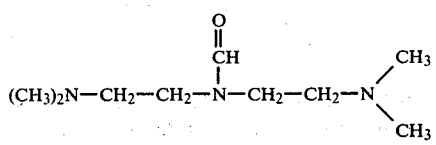

pyridine, quinoline and their methyl substituted derivatives used alone or as mixtures with the above-mentioned tertiary bases. Compounds of this group which are also interesting catalysts include Mannich bases such as the compound represented by the following formula:

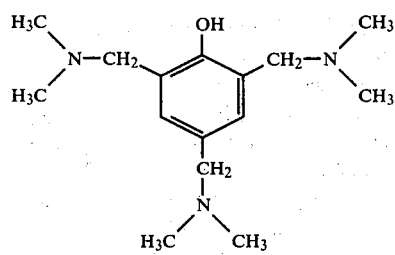

Another interesting group of catalysts are the known mono- and polyepoxides, e.g. those of the following constitution:

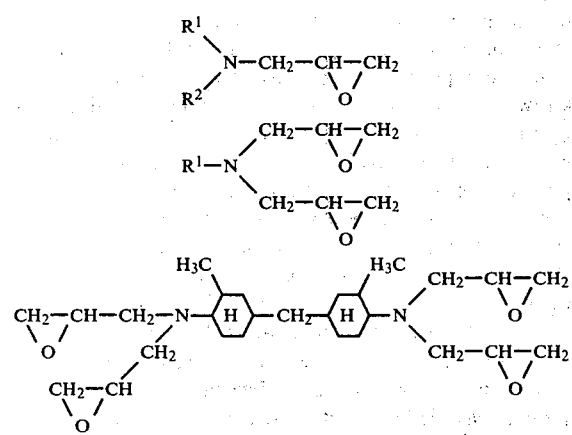

Examples of quaternary ammonium bases which are also useful catalysts according to the invention include 10 to 20% solutions of:

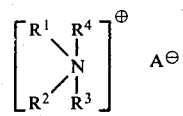

in alcohols such as methanol or ethanol; and

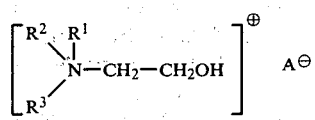

wherein $R^1$, $R^2$, $R^3$ and $R^4$ represent alkyl, cycloalkyl or aralkyl groups having from 1 to 10 carbon atoms, preferably methyl, ethyl, cyclohexyl or benzyl; and A represents a basic anion, preferably a hydroxyl, acetate or phenolate ion, most preferably a cyanide ion.

Examples of ternary sulphonium bases which are useful catalysts include those corresponding to the following formulae:

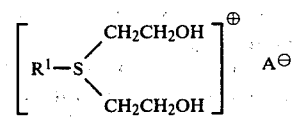

and

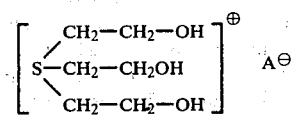

in which $R^1$ and $A^{\ominus}$ have the meaning mentioned above.

Of course, a cross-linked insoluble resin, for example a cross-linked polystyrene, bearing quaternary ammonium base groups or ternary sulphonium base groups may also be mentioned as an organic basic catalyst according to the invention.

Among the inorganic catalysts, sodium hydroxide, sodium cyanide, sodium phenolate and sodium methylate are preferred.

Among the organic basic catalysts, the following are particularly preferred: Dimethylcyclohexylamine, triethylamine, the cyanides of quaternary ammonium bases such as tetramethylammonium cyanide and tetraethylammonium cyanide and quaternary ammonium compounds which have a betaine-like character, such as choline, which can be prepared in known manner from trimethylamine, ethylene oxide and 1 mol of water. In this group, choline cyanide is particularly preferred. Among the insoluble basic catalysts, there may also be used strongly basic ion exchange resins, e.g. those having groups corresponding to the following formulae:

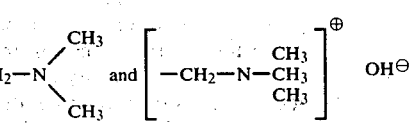

bound to an insoluble polystyrene matrix. When such ion exchange catalysts are used, the reaction according to the invention is slower by a factor of about 50 because the large sugar molecules diffuse relatively slowly to the basic centers of the matrix.

Cyanides, both of alkali metals and of quaternary ammonium compounds, are particularly preferred when exceptionally pure and colorless branched sugars are to be produced with high yields.

The source of formaldehyde used for carrying out the process according to the invention is generally an aqueous and/or alcoholic formalin solution and/or paraformaldehyde dispersion containing from 10 to 70% by weight, preferably from 20 to 65% by weight, most preferably from 30 to 50% by weight of formaldehyde; and/or compounds which are capable of transmethylolation, such as N-methylol-caprolactam, N-methylolpyrrolidone, N-methylolated ureas and thioureas, methylolated N,N-dimethylurea, methylolated dicyandiamide, methylolated melamine, i.e. N-methylol compounds of aminoplast monomers in general. The reaction according to the invention may, if desired, also be carried out in the presence of phenols, naphthols or bisphenol A, i.e. compounds which are capable of phenoplast formation. In this case, the sugars according to the invention are obtained as mixtures with hydroxybenzyl alcohols or hydroxybenzylpolyalcohols which are not capable of transmethylolation and which may be easily, subsequently etherified, if desired, with the alcoholic hydroxyl groups of the new sugar derivatives by acidification to pH=2-4.

The process according to the invention may, of course, also be carried out with virtually anhydrous hemiacetals of formaldehyde with monohydric alcohols such as methanol, ethanol and propanol or also with hemiacetals of polyhydric alcohols such as ethylene glycol, propylene glycol, diethylene glycol, triethylene glycol, glycerol, N-methyl-diethanolamine, dimethylethanolamine or triethanolamine. In cases where basic alcohol-hemiacetals are used, the additional use of basic catalysts is, of course, unnecessary.

A particularly preferred source of formaldehyde is the hot synthesis gases which are obtained from the large scale industrial production of formaldehyde. These gases may be used directly for α-C-methylolation reactions and α,α'-C-polymethylolation reactions. When these synthesis gases are used, solutions of the reducing sugars to be modified, adjusted to the pH required for the invention, are used as absorption liquids for the formaldehyde. For this purpose, the sugar solutions are preferably passed in counter-current to the hot synthesis gases and the addition reaction is either carried out at the same time, preferably at about 50° to 95° C. and a pH of 8 to 9, or, if the absorption liquid contains no catalyst, the methylolation reaction is initiated by subsequent addition of the catalysts described above.

Any of the synthesis gases obtained from the commercial production of formaldehyde may be used in the process according to the invention. Examples of large scale industrial formaldehyde production processes include the dehydration of methanol or oxidation of methanol on suitable catalysts, for example silver or iron molybdenum oxide in the presence of air, optionally water vapor and formaldehyde exhaust gases; and the oxidation of methane or ethylene or higher olefines or dimethylether with air or oxygen or oxygen-containing gases on suitable catalysts. These commercial synthesis gases generally contain from 20 to 70 volume % of nitrogen as their main constituent, from 1 to 20 volume % of formaldehyde and from 1 to 10 volume % of carbon dioxide. In most cases, depending on the manufacturing process, they also contain substantial quantities of water vapor, residues of air, carbon monoxide, hydrogen and residues of starting materials or by-products such as methanol, methane, ethylene, higher olefines, methylformate, dimethyl ether and acetals and hemiacetals of formaldehyde. Since sugars frequently tend to turn brown in the presence of oxygen, for the purpose of the invention, it is preferred to use synthesis gases which are free from oxygen.

In other respects, however, the synthesis gases obtained from the large scale production of formaldehyde may be used in the crude state for the process according to the invention, that is to say without any previous purification. This is particularly advantageous from an economic point of view. The large quantities of carbon dioxide normally present in the synthesis gases also do not interfere with the methylolation reaction according to the invention.

In the variation in which synthesis gases are used as the source of formaldehyde, the process may be carried out either at normal pressure, at excess pressure or at reduced pressure (with chilled synthesis gases). The absorption liquid, consisting of a solution of the reducing sugar to be methylolated is introduced into a suitable absorption column and the synthesis gas is introduced continuously or intermittently at a temperature of about 90° to 250° C., preferably 100° to 140° C., into the absorption liquid which is maintained at about 70° to 110° C., preferably 80° to 85° C. The absorption liquid may also contain from about 10 to 60% by weight of the monohydric and polyhydric alcohols with molecular weights of from 32 to 10,000 and from 1 to 50% by weight of aminoplast or phenoplast monomers, phosphites and/or aldehydes and ketones which are capable of α-methylolation, as will be described below.

In the one variation of the process, the synthesis gas is passed through a column filled with absorption liquid. To accelerate the exchange of material between the two phases, the absorption column preferably contains filling bodies of known type which have a large surface area, such as Raschig rings, saddle rings, sieve bottoms or fine meshed wire netting. The synthesis gas is passed through the absorption column until the absorption liquid is saturated, i.e. until the inert gases leaving at the top of the column are accompanied by substantial quantities of formaldehyde. The absorption liquid preferably already contains the catalyst for the process according to the invention so that the methylolation reaction can already begin during the absorption of the formaldehyde. The advantage of this method is that it allows a given volume of absorption liquid to absorb a larger quantity of formaldehyde. It is, of course, also possible according to the invention to introduce the synthesis gases into a catalyst-free absorption liquid until saturation point is reached and only then to start the reaction by adding the catalyst.

It is particularly economical, as already mentioned, to carry out the process according to the invention continuously. For this purpose, a circulation of absorption liquid is maintained and the liquid is advantageously carried in counter-current to the hot synthesis gases. In this preferred variation of the process, it is also advantageous for the purpose of facilitating the exchange of materials to use absorption columns in the form of known columns with filling bodies, bubble trays or perforated bottoms or trickle film columns. Bubble columns may, of course, also be used for the process according to the invention. The average residence time of the formaldehyde-containing synthesis gases in the absorption columns both for the continuous and for the batchwise variation of the process according to the invention is generally from 0.3 to 10 seconds, and preferably from 0.6 to 3 seconds.

FIG. 1 represents a simplified schematic representation of an apparatus suitable for carrying out the process according to the invention continuously. Hot synthesis gas containing formaldehyde is introduced at 1 into the absorption column A filled with absorption liquid. The reducing sugar solution and any additives (e.g. catalyst, base, alcohols, aldolizable aldehydes and ketones, aminoplast formers, and the like) may be introduced at 2. The absorption liquid is circulated by the pump B and carried in counter-current to the synthesis gas. The gases freed from formaldehyde but containing water vapor leave the absorption column at 3. C represents a residence time vessel which can be heated or cooled and in which the methylolation reaction may take place. Absorption liquid containing part of the reaction product and residues of formaldehyde is continuously removed at 4 and passed through another dwell time vessel D. In the case where the absorption column contains no or insufficient catalyst to complete the methylolation reaction, additional catalyst and additional additives, for example aminoplast former and the like, may be introduced at 5. The reaction product leaves the apparatus at 6.

In the continuous method it is also possible, as mentioned above, to add the basic catalyst to the absorption liquid (about 0.01 to 10% by weight, preferably 0.3 to 2% by weight) so that absorption of formaldehyde and chemical addition of formaldehyde to reducing sugar take place simultaneously. Alternatively, the catalyst may be added after removal of the product (for example in position 5 of FIG. 1) so that methylolation takes place outside the circulation.

If the absorption liquid does not contain any basic catalyst, the hemiacetals of the hydroxyl compounds present in the absorption liquid, for example those corresponding to the following formula:

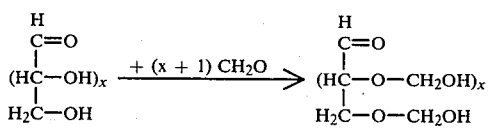

first form in equilibrium with the formaldehyde dissolved in the water. Since the dissociation equilibrium between these hemiacetals and free formaldehyde is established very rapidly in the presence of water, the branched sugar is very rapidly formed from such mixtures after the addition of catalyst at 70° to 110° C., preferably at 80° to 85° C.

If the methylolation reaction partly or completely takes place outside the circulation of absorption liquid, it may, according to the invention, be carried out, for example, in continuously operating cascades of stirrer vessels. This variation of the process allows the residual formaldehyde content to be adjusted exactly by varying the residence time in the individual stirrer vessels of the cascade. Instead of using cascade stirrer vessels, the reaction of formaldehyde according to the invention may also be carried out in reaction tubes, for example in tubular coils under pressure (about 5 to 150 bar, preferably 10 to 70 bar) at elevated temperatures (preferably 105° to 140° C.).

The quantity of formaldehyde used may vary within wide limits in the process according to the invention. As a general rule from 0.05 to 10 mol, preferably from 0.2 to 5 mol, most preferably from 1.0 to 1.5 mol of formaldehyde is used per equivalent of $\alpha$- or $\alpha'$-hydrogen atoms (i.e. hydrogen atoms which can be substituted by a methylol group) of the reducing sugar. If less than the equivalent quantity of formaldehyde is used, mixtures of $\alpha$- and/or $\alpha'$-methylolated sugars and unmodified sugars are obtained. Solutions of such mixtures have the advantage of greatly reduced viscosity and reduced tendency to crystallization compared with the starting solutions. Mixtures of the branched sugars according to the invention with unmodified sugars (in particular glucose and/or saccharose) in proportions by weight in the range of from 5:95 to 95:5, preferably from 20:80 to 80:20, are particularly advantageous.

If, on the other hand, a large excess of formaldehyde is used in the process according to the invention (e.g. about 5 to 6 times the quantity theoretically required for methylolation), hemiacetals of the branched sugars according to the invention are obtained after dehydration of the reaction mixture (preferably in a vacuum of about 0.05 to 16 Torr). These hemiacetals may, if desired, be converted into novel, straight chain or branched chain whole acetals or polyacetals by acidification (pH 1 to 4).

If, exceptionally pure branched sugars according to the invention are to be produced, it is preferred to use from 1.18 to 1.20 mol of formaldehyde per equivalent of $\alpha$- or $\alpha'$-hydrogen atom of reducing sugar, and to stop the reaction by cooling and/or neutralization when the reaction mixture has a residual formaldehyde content of about 0.3 to 0.9% by weight.

The process according to the invention may, thus, be carried out continuously or intermittently, at reduced pressure or at excess pressure. According to one particular embodiment, the methylolation reaction is carried out in a cascade of stirrer vessels. By varying the residence time and the pH in the individual stirrer vessels in this embodiment of the invention, the degree of addition of formaldehyde to the $\alpha$- and $\alpha'$-carbon atoms of the reducing sugars (preferably gluscose, fructose, maltose, lactose cellobiose and mixtures thereof, invert sugars, types of honey, "isosyrups", hydrolyzed cane sugar, hydrolyzed starch and saccharified cellulose) can be adjusted exactly. It is therefore also possible as noted above to carry out only partial C-methylolation reactions on a naturally occurring sugar and produce mixtures consisting, for example, of 1 mol of $\alpha$-methylolated glucose and 1 mol of unreacted glucose, whereby the tendency of crystallization of the dehydrated mixture is reduced. The viscosity of the sugar mixtures which have a low water content can be greatly reduced.

It should be particularly mentioned that when the pH is controlled according to the invention and the preferred basic catalysts are used in the process according to the invention, crossed Cannizzaro reactions of formaldehyde are very powerfully suppressed and the sugars can surprisingly be obtained in yields of 95 to 98%, unaccompanied by dehydration reactions or, to any significant extent, crossed Cannizzaro reactions or aldo condensations of the sugars with each other.

The C-methylolation reactions according to the invention do not generally require inactivation of catalyst because the preferred, small quantities of catalyst used are in most cases inactivated towards the end of the reaction, at a residual formaldehyde content of the new, branched sugars of about 0.3 to 0.9% by weight, by small quantities of formic acid formed or by saccharic acids, and the pH therefore generally falls to somewhere in the range of 7-6.8 towards the end of the reaction. If desired, however, the reaction products may be freed from salt on acid and basic ion exchange resins.

According to the invention, it is preferred, as mentioned above, to operate in the absence of metal ions, in particular of polyvalent metal ions, and in other words, it is preferred to use organic bases as catalysts. The reason for this is that polyvalent metal ions catalyze the condensation of formaldehyde to polyhydroxyaldehydes and ketones (so-called formose synthesis). If the $\alpha,\alpha'$-C-methylolation according to the invention is carried out with excess formaldehyde, based on all the aldo and keto equivalents of the natural sugar or sugar derivative used, in the presence of metal catalysts (such as calcium hydroxide, lead hydroxide, calcium oxide, lead oxide, calcium phenolate, calcium carbonate, thallium hydroxide, and the like), mixtures of $C_3$–$C_9$ polyhydroxyaldehydes, polyhydroxy ketones and polyalcohols (formoses) in the form of their optically inactive D,L-racemates are therefore formed in addition to the $\alpha,\alpha'$-C-methylolated sugars according to the invention.

It is often advantageous to carry out the reaction according to the invention in the presence of low molecular, monohydric or, preferably, polyhydric alcohols in order to obtain relatively low viscosity, very fluid reaction products which can easily be dehydrated in a thin layer evaporator. Relatively high molecular polyhydroxyl compounds (molecular weight up to 10,000) may also be included, particularly if synthesis gases containing formaldehyde are used. Examples of useful monohydric and polyhydric alcohols include methanol, ethanol, propanol, butanol, amyl alcohol and the polyhydroxyl compounds which are described below in connection with the production of polyurethanes, in particular ethylene glycol, glycerol, trimethylolpropane, formitols, diethylene glycol, triethylene glycol, propanediol-(1,2), propanediol-(1,3), butanediol-(1,4), N-methyl-diethanolamine, N-ethyl-diethanolamine, ethoxylated and propoxylated ethylene diamine, ethoxylated and propoxylated hydrazine and substituted hydrazine (e.g., N,N-dimethyl- or diethyl-hydrazine) as well as water-insoluble but emulsifiable polyhydric alcohols such as castor oil, hexanetriol and 2-ethylhexanediol-(1,3) and ethoxylation and propoxylation products of all the above-mentioned monohydric and polyhydric alcohols.

The methylolation of reducing sugars according to the invention may also be carried out in the presence of other compounds which are capable of being C- or N-methylolated. More highly fluid and more readily dehydrated products which react more rapidly with polyisocyanates are thereby obtained, which are suitable for the production of flame resistant polyurethanes. Examples of such reactive additives include, quite generally, primary and/or secondary amines and/or substances suitable for aminoplast or phenoplast formation and their methylolation products, for example as described in German Offenlegungsschriften Nos. 2,324,134 and 2,639,254. The following are specific examples: Aniline, urea, symmetrically or asymmetrically substituted ureas such as N,N-dimethyl- (or -diethyl- or dibutyl-)urea, thiourea, dicyandiamide, melamine, oxamide, ethylene urea, ε-caprolactam, pyrrolidone-(2), acetylenediurein and the N-methylol compounds of all these aminoplast monomers, phenols and methylolated phenols.

Aldehydes and ketones which do not have the character of sugars but are capable of being α- or α'-methylolated may also be used in the process according to the invention. Examples of such aldehydes and ketones include acetaldehyde, acetone, propionaldehyde, butyraldehyde, isobutyraldehyde, methyl ethyl ketone, cyclopentanone, cyclohexanone, mesityl oxide, isophorone, acetophenone and their methylol derivatives obtainable by alkaline catalyzed partial aldolization with formaldehyde on the C-atom in the α-position to the keto group. Compounds corresponding to the following formulae are examples:

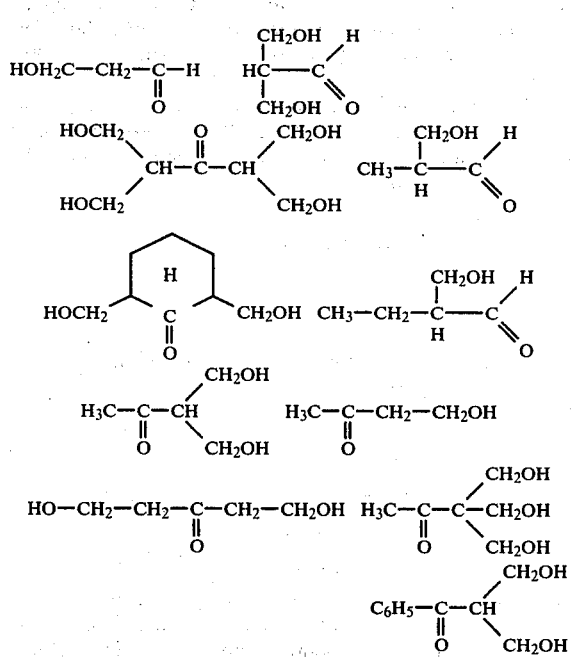

By-products of the commercial production of trimethylolpropane from butyric acid aldehyde and formaldehyde, such as 2-ethylacrolein, may also be used. 2-Ethylacrolein, for example, is converted into 2,2-dimethylolalkanol in the presence of tertiary amine catalysts such as triisobutylamine in accordance with the following reaction scheme:

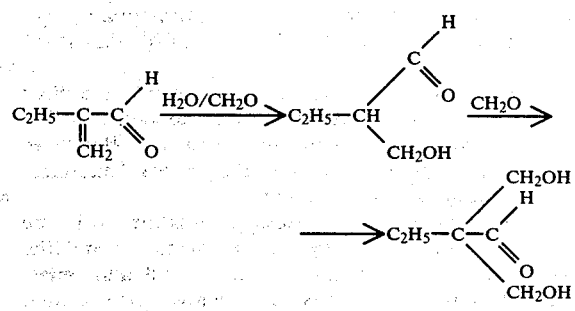

These methylolated aldehydes and ketones also have the advantageous effect of lowering the viscosity of the sugar derivatives prepared according to the invention.

Alkylphosphites such as dimethylphosphite, diethylphosphite or triethylphosphite may also be included in the methylolation reaction according to the invention. In that case, α-hydroxymethyl-phosphonic acid esters or transesterification products with the hydroxyl groups of the sugars are formed by an alkaline catalyzed reaction with formaldehyde. Other CH-acidic compounds, such as malonic acid esters or acetoacetic acid esters react similarly. Sugars modified with alkylphosphites in particular are valuable starting materials for the production of flame resistant polyurethane foams. It may be regarded as particularly surprising that the branched sugars according to the invention are soluble in the above-mentioned phosphites while glucose and other monosaccharides as well as cane sugar are insoluble in these phosphites. It is surprisingly found that solutions which have a much lower viscosity than those of unmodified sugars and having improved emulsifiability or miscibility with various low molecular and higher molecular polyhydroxyl compounds are obtained.

In the sugars modified with dialkylphosphite, equilibria are established between free dialkylphosphite, hydroxymethanephosphonic acid esters having the following constitution:

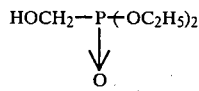

and α-hydroxyphosphonic acid esters having the following constitutions:

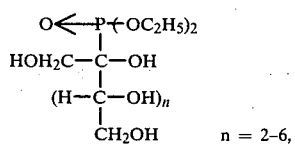

n = 2–6, the equilibria depending on the temperature. At elevated temperatures, above about 35° C., and particularly in the presence of catalyst quantities of inorganic bases or preferably tertiary amines such as triethylamine or dimethylbenzylamine, these compounds enter into molecular rearrangement reactions and transesterification reactions with the elimination of alcohol. Cyclic phosphites of the sugars are thus formed or, via intermolecular linkage of sugars, higher molecular polyphosphites or sugar esters of hydroxymethylphosphonic acid may be formed. Any degree of transesterification can be obtained according to the quantity of alcohol split off, so that the viscosities may vary, e.g. from about 300 mPas at 20° to about 110,000 mPas at 20° C.

All the formaldehyde reactive compounds described above may, if desired, be added after the methylolation reaction according to the invention in order to bind free formaldehyde in the products of the process if an excess of formaldehyde has been used.

The commercially interesting mixtures of the branched sugars according to the invention and the above described, optionally methylolated aminoplast and phenoplast monomers, aldehydes, ketones and phosphites in proportions by weight in the range of from 99:1 to 5:95, preferably from 98:2 to 50:50, most preferably from 95:5 to 70:3, also form part of the invention. Examples include mixtures of α- and α'-methylolated sugars and dimethyl- and/or diethylphosphite, caprolactam, N-methylolated caprolactam, pyrrolidone, urea, melamine, dicyandiamide and dimethyl- and diethylurea, condensation products of 1 mol of aniline and 1 to 5 mols of formaldehyde, mono-, di- and trimethylolphenol, resoles, and mono- and polymethylolated low molecular aldehydes and ketones such as cyclohexanone, acetaldehyde, propionaldehyde, n-butyraldehyde, acetone, methyl ethyl ketone and methylisobutyl ketone.

The new branched sugars according to the invention can be used in numerous reactions resulting in valuable commercial sugar derivatives, e.g. hydrogenation to branched alcohols; OH⊖- or H⊕-catalyzed reactions, preferably using Lewis acids as catalysts, with ethylene oxide, propylene oxide or epichlorohydrin to form polyethers; preparation of polyesters; intermolecular and intramolecular acetal formation; acylation reactions with acetic anhydride, ketene or diketene; cyanoethylation with acrylonitrile followed by hydrogenation reactions; preparation of non-ionogenic surface active compounds, e.g. by reaction with fatty acids or long chain aliphatic monoisocyanates.

One interesting variation of the process according to the invention consists in binding the residual formaldehyde by acidification to a pH of about 1 to 3, whereby intramolecular and intermolecular acetals are formed, accompanied by elimination of water, if necessary in the presence of boric acid as catalyst.

Intermolecular acetal formation (idealized):

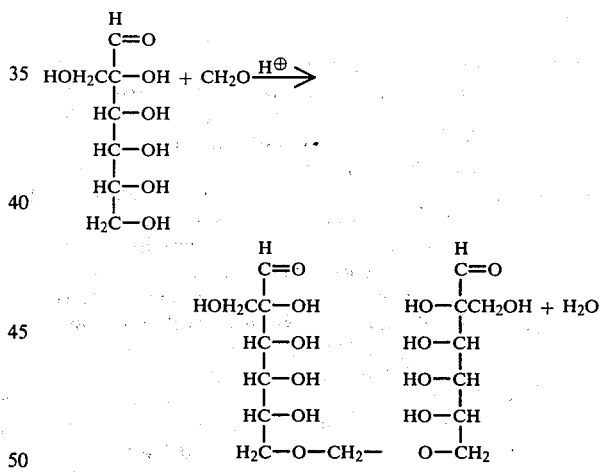

Such end products, which have been modified by acetal formation have low viscosities, whereby their miscibility or emulsifiability with the higher molecular polyhydroxyl compounds used in the production of polyurethane is substantially improved.

Polyhydric alcohols can easily be obtained from the branched sugars according to the invention by reduction by known methods if desired. Thus, for example, the aqueous solution of sugars obtained can be directly reduced with sodium borohydride at room temperature. Reduction may also be carried out by other methods, e.g. electrolytically. Catalytic hydrogenation with hydrogen is also possible. Any known method for the reduction of sugars to sugar alcohols may be employed for this purpose. Hydrogenation with Raney nickel used in quantities of from 5 to 20% by weight, based on the sugar to be reduced, at hydrogen pressures of from 50 to 200 kg/cm² and at a temperature of from 20° to 200° C. is particularly suitable but catalysts containing nickel, cobalt, copper, platinum, rhodium or palladium on inert carriers may be used with similarly good results.

The branched sugars prepared according to the invention are interesting solubilizing agents or solvents for sparingly soluble metal hydroxides, for example the hydroxides of calcium, barium, rare earths, strontium, beryllium, zinc, magnesium, lead, thallium, divalent chromium, divalent manganese, divalent and trivalent iron, aluminum, divalent tin and divalent and trivalent cobalt. Such sugar solutions enriched with various metal hydroxides are valuable catalysts for the reaction of isocyanates with water or polyhydroxyl compounds.

The branched sugars according to the invention are in many cases uniform compounds. They are also suitable, for example, for the synthesis of biologically active substances, flame retarding agents and cross-linked high polymers of hitherto unknown constitution resembling humic acid.

The products obtained by the process according to the invention are suitable in particular as polyol components for the production of polyurethane resins.

This invention thus also relates to a process for the production of cellular or non-cellular polyurethane resins by the reaction of
(A) polyisocyanates with
(B) low molecular polyhydroxyl compounds and optionally
(C) relatively high molecular polyhydroxyl compounds, other chain lengthening agents, blowing agents, catalysts and other known additives, characterized in that the derivative of reducing sugars produced according to the invention and/or their hydrogenation products and/or their alkoxylation products are used as component (B).

To produce the polyurethane resins of the invention, aliphatic, cycloaliphatic, araliphatic, aromatic and heterocyclic polyisocyanates such as those described e.g. by W. Siefken in Justus Liebigs Annalen der Chemie, 562, pages 75 to 136 are used. Examples include those corresponding to the following formula:

$$Q(NCO)_n$$

in which
n=2–4, preferably 2, and
Q represents an aliphatic hydrocarbon group having from 2–18, preferably 6–10 carbon atoms,
a cycloaliphatic hydrocarbon group having from 4–15, preferably 5–10 carbon atoms,
an aromatic hydrocarbon group having from 6–15, preferably 6–13 carbon atoms or an araliphatic hydrocarbon group having from 8–15, preferably 8–13 carbon atoms.

Specific examples include: ethylene diisocyanate; 1,4-tetramethylene diisocyanate; 1,6-hexamethylene diisocyanate; 1,12-dodecanediisocyanate; cyclobutane-1,3-diisocyanate; cyclohexane-1,3- and 1,4-diisocyanate and mixtures of these isomers; 1-isocyanato-3,3,5-trimethyl-5-isocyanatomethyl-cyclohexane (German Auslegeschrift No. 1,202,785, U.S. Pat. No. 3,401,190); 2,4- and 2,6-hexahydrotolylene diisocyanate and mixtures of these isomers; hexahydro-1,3- and/or 1,4-phenylene diisocyanate; perhydro-2,4'- and/or 4,4'-diphenylmethane diisocyanate; 1,3- and 1,4-phenylene diisocyanate; 2,4-and 2,6-tolylene diisocyanate and mixtures of these isomers; diphenylmethane-2,4'- and/or 4,4'-diisocyanate; naphthylene-1,5-diisocyanate; triphenylmethane-4,4',4"-triisocyanate; polyphenyl-polymethylene polyisocyanates which may be obtained by aniline-formaldehyde condensation followed by phosgenation and which have been described e.g. in British Pat. Nos. 874,430 and 848,671; m- and p-isocyanatophenylsulphonyl isocyanates as described in U.S. Pat. No. 3,454,406; perchlorinated aryl polyisocyanates as described e.g. in German Auslegeschrift No. 1,157,601 (U.S. Pat. No. 3,277,138); polyisocyanates containing carbodiimide groups as described in German Pat. No. 1,092,007 (U.S. Pat. No. 3,152,162) and in German Offenlegungsschriften Nos. 2,504,400; 2,537,685 and 2,552,350; norbornane diisocyanates as described in U.S. Pat. No. 3,492,330 polyisocyanates with allophanate groups as described, for example, in British Pat. No. 994,890; Belgian Pat. No. 761,626 and Netherlands Patent Application No. 7,102,524; polyisocyanates with isocyanurate groups as described e.g. in U.S. Pat. No. 3,001,973; German Pat. Nos. 1,022,789; 1,222,067 and 1,027,394 and in German Offenlegungsschriften Nos. 1,929,034 and 2,004,048; polyisocyanates with urethane groups as described, for example, in Belgian Pat. No. 752,261 or in U.S. Pat. Nos. 3,394,164 and 3,644,457; polyisocyanates with acylated urea groups as described in German Pat. No. 1,230,778; polyisocyanates with biuret groups as described e.g. in U.S. Pat. Nos. 3,124,605; 3,201,372 and 3,124,605 and in British Pat. No. 889,050; polyisocyanates prepared by telomerization reactions as described, for example, in U.S. Pat. No. 3,654,106; polyisocyanates with ester groups as described in British Pat. Nos. 965,474 and 1,072,956; U.S. Pat. No. 3,567,763 and German Pat. No. 1,231,688; reaction products of the above-mentioned isocyanates with acetals as described in German Pat. No. 1,072,385 and polyisocyanates containing polymeric fatty acid esters as described in U.S. Pat. No. 3,455,883. The distillation residues obtained from the commercial production of isocyanates and still containing isocyanate groups may also be used, optionally dissolved in one or more of the abovementioned polyisocyanates. Mixtures of the abovementioned polyisocyanates may also be used.

As a rule, it is particularly preferred to use readily available polyisocyanates such as 2,4- and 2,6-tolylene diisocyanate and mixtures of these isomers ("TDI"); polyphenyl-polymethylene polyisocyanates obtainable by aniline-formaldehyde condensation followed by phosgenation ("crude MDI"); and polyisocyanates containing carbodiimide, urethane, allophanate, isocyanurate, urea or biuret groups ("modified polyisocyanates"), especially those modified polyisocyanates which are derived from 2,4- and/or 2,6-tolylene diisocyanate or from 4,4'- and/or 2,4'-diphenylmethane diisocyanate.

Also useful in producing polyurethane resins are compounds having at least two isocyanate reactive hydrogen atoms and molecular weights generally of from 400 to 10,000. These compounds may contain amino groups, thiol groups, carboxyl groups or hydroxyl groups. Preferably compounds containing hydroxyl groups, in particular from 2 to 8 hydroxyl groups, especially those with a molecular weight of from 500 to 7000, preferably from 1000 to 5000 are used. Examples include polyesters, polyethers, polythioethers, polyacetals, polycarbonates and polyester amides containing at least 2, generally 2 to 8, preferably 2 to 4 hydroxyl groups, such as the known compounds used for the production of homogeneous and cellular polyurethanes. Suitable polyesters with hydroxyl groups include e.g. reaction products of polyhydric alcohols and polybasic carboxylic acids. Instead of free polycarboxylic acids there may, of course, also be used the corresponding polycarboxylic acid anhydrides or corresponding polycarboxylic acid esters of lower alcohols or mixtures thereof for preparing the polyesters. The polycarboxylic acids may be aliphatic, cycloaliphatic, aromatic and/or heterocyclic and they may be substituted, e.g. by halogen atoms, and/or they may be unsaturated.

The following are examples of such carboxylic acids and their derivatives: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimerized and trimerized unsaturated fatty acids optionally mixed with monomeric unsaturated fatty acids such as oleic acid; dimethyl terephthalate and terephthalic acid-bis-glycol esters. The following are examples of suitable polyhydric alcohols: ethylene glycol, propylene glycol-(1,2) and -(1,3), butylene glycol-(1,4), and -(2,3), hexanediol-(1,6), octanediol-(1,8), neopentylglycol, 1,4-bis-hydroxymethylcyclohexane, 2-methyl-1,3-propanediol, glycerol, trimethylolpropane, hexanetriol-(1,2,6), butanetriol-(1,2,4), trimethylolethane, pentaerythritol, quinitol, mannitol and sorbitol, formitol, methylglycoside, diethylene glycol, triethyleneglycol, tetraethylene glycol and higher polyethylene glycols, dipropylene glycol and higher polypropylene glycols, and dibutylene glycol and higher polybutylene glycols. The polyesters may also contain a proportion of carboxyl end groups. Polyesters of lactones such as ε-caprolactone or of hydroxycarboxylic acids such as ω-hydroxycaproic acid may also be used.

The polyethers which may be used according to the invention and which have at least 2, generally 2 to 8, preferably 2 to 3 hydroxyl groups are also known and are prepared, for example, by the polymerization of epoxides such as ethylene oxide, propylene oxide, butylene oxide, tetrahydrofuran, styrene oxide or epichlorohydrin, either each on its own, e.g. in the presence of Lewis catalysts such as boron trifluoride or by addition of these epoxides, preferably ethylene oxide and propylene oxide, either as mixtures or successively, to starting components having reactive hydrogen atoms. Suitable starting components include water, ammonia, alcohols such as ethylene glycol, propylene glycol-(1,3) or -(1,2), trimethylolpropane, glycerol, sorbitol, and 4,4'-dihydroxydiphenylpropane, and amines such as aniline, ethanolamine or ethylene diamine. It is in many cases preferred to use polyethers which contain predominant amounts of primary hydroxyl groups (up to 90% by weight, based on all the hydroxyl groups present in the polyether). Polybutadienes containing hydroxyl groups are also suitable for the purpose of the invention.

Particularly to be mentioned among the polythioethers are the condensation products obtained by reacting thiodiglycol on its own and/or with other glycols, dicarboxylic acids, formaldehyde, amino-carboxylic acids or amino alcohols. The products obtained are polythio mixed ethers, polythio ether esters or polythio ether ester amides, depending on the co-components.

Suitable polyacetals include, for example, the compounds which can be prepared from glycols such as diethylene glycol, triethylene glycol, 4,4'-dioxethoxydiphenyl dimethylmethane, hexanediol and formaldehyde. Suitable polyacetals for the purpose of the invention may also be prepared by the polymerization of cyclic acetals, e.g. trioxane, (German Offenlegungsschrift No. 1,694,128).

The polycarbonates with hydroxyl groups used may be of the kind known per se, for example those which can be prepared by the reaction of diols such as propane-(1,3), butanediol-(1,4) and/or hexanediol-(1,6), diethylene glycol, triethylene glycol tetraethylene glycol or thiodiglycol with diarylcarbonates, e.g. with diphenylcarbonate or phosgene. (German Auslegeschriften Nos. 1,694,080; 1,915,908; 2,221,751; German Offenlegungsschrift No. 2,605,024).

Suitable polyester amides and polyamides include, for example, the predominantly linear condensates prepared from polyvalent saturated and unsaturated carboxylic acids or their anhydrides and polyvalent saturated and unsaturated amino alcohols, diamines, polyamines and mixtures thereof.

Polyhydroxyl compounds already containing urethane or urea groups and modified or unmodified natural polyols such as castor oil or carbohydrates, e.g. starch may also be used. Addition products of alkylene oxides and phenol formaldehyde resins or of alkylene oxides and urea formaldehyde resins are also suitable for the purpose of the invention.

The polyhydroxyl compounds mentioned above may be modified in various ways before they are used in the polyisocyanate polyaddition process. Thus, as described in German Offenlegungsschriften Nos. 2,210,839 (U.S. Pat. No. 3,849,515) and 2,544,195, a mixture of various polyhydroxyl compounds (e.g. of a polyether polyol and a polyester polyol) may be condensed by etherification in the presence of a strong acid to a relatively high molecular polyol consisting of various segments linked by ether bridges. Furthermore, amide groups may be introduced into the polyhydroxyl compounds as described in German Offenlegungsschrift No. 2,559,372, for example, or triazine groups may be introduced by a reaction with polyfunctional cyanic acid esters as described in German Offenlegungsschrift No. 2,620,487. Polyhydroxyl compounds containing guanidine, phosphonoformamidine or acylurea groups are obtained by the reaction of a polyol with less than the equivalent quantity of a diisocyanatocarbodiimide, followed by reaction of the carbodiimide group with an amine, amide, phosphite or carboxylic acid (German Offenlegungsschriften Nos. 2,714,289; 2,714,292 and 2,714,293). In some cases, it is of particular interest to convert the relatively high molecular polyhydroxyl compounds completely or partly into the corresponding anthranilic acid esters by a reaction with isatoic acid anhydride, as described in German Offenlegungsschriften Nos. 2,019,432 and 2,619,840 or in U.S. Pat. Nos. 3,808,250; 3,975,428 and 4,016,143. Relatively high molecular compounds with aromatic amino end groups are thereby obtained.

According to German Offenlegungsschrift No. 2,546,536 and U.S. Pat. No. 3,865,791, relatively high molecular weight compounds carrying amino end groups are obtained by the reaction of isocyanate prepolymers with hydroxyl-containing enamines, aldimines or ketimines followed by hydrolysis. Other methods of preparation for relatively high molecular weight compounds with amino end groups or hydrazide end groups are described in German Offenlegungsschrift No. 1,694,152 (U.S. Pat. No. 3,625,871).

According to the invention, polyhydroxyl compounds which contain high molecular polyadducts or polycondensates or polymers in a finely dispersed or dissolved form may also be used. Polyhydroxyl compounds of this type are obtained, for example, when polyaddition reactions, e.g. reactions between polyisocyanates and aminofunctional compounds, or polycondensation reactions, e.g. between formaldehyde and phenols and/or amines, are carried out in situ in the above-mentioned hydroxyl compounds. Processes of this kind have been described, for example, in German Auslegeschriften Nos. 1,168,075 and 1,260,142 and in German Offenlegungsschriften Nos. 2,324,134; 2,423,984; 2,512,385; 2,513,815; 2,550,796; 2,550,797; 2,550,833; 2,550,862; 2,633,293 and 2,639,254. These compounds may also be obtained by mixing a previously prepared aqueous polymer dispersion with a polyhydroxyl compound and then removing water from the mixture as described in U.S. Pat. No. 3,869,413 or German Offenlegungsschrift No. 2,550,860.

Polyhydroxyl compounds modified with vinyl polymers are also suitable for the process according to the invention. These may be obtained, for example, by the polymerization of styrene or acrylonitrile in the presence of polyethers (U.S. Pat. Nos. 3,383,351; 3,304,273; 3,523,093 and 3,110,695; German Auslegeschrift No. 1,152,536) or polycarbonate polyols (German Pat. No. 1,769,795, U.S. Pat. No. 3,637,909). Synthetic materials with exceptionally high flame resistance are obtained by using polyether polyols which have been modified as described in German Offenlegungsschriften Nos. 2,442,101; 2,644,922 and 2,646,141 by graft polymerization with vinyl phosphonic acid esters and possibly also with (meth)acrylonitrile, (meth)acrylamide or OH functional (meth)acrylic acid esters. Polyhydroxyl compounds into which carboxyl groups have been introduced by the radical graft polymerization with unsaturated carboxylic acids and optionally with other olefinically unsaturated monomers (German Offenlegungsschriften Nos. 2,714,291; 2,739,620 and 2,654,746) are particularly advantageously used in combination with mineral fillers.

When modified polyhydroxyl compounds of the type mentioned above are used as starting components for the polyisocyanate polyaddition process, the polyurethanes obtained have in many cases substantially improved mechanical properties.

Representatives of the many compounds which can be used according to the invention have been described, e.g. in High Polymers, Vol. XVI, "Polyurethanes, Chemistry and Technology" by Saunders-Frisch, Interscience Publishers, New York, London, Volume I, 1962, pages 32–42 and pages 44–54 and Volume II, 1964, pages 5–6 and 198–199; and in Kunststoff-Handbuch, Volume VII, Vieweg-Höchtlen, Carl-Hanser-Verlag, Munich, 1966, e.g. on pages 45–71. The above-mentioned compounds with a molecular weight of from 400 to 10,000 containing at least two isocyanate reactive hydrogen atoms may, of course, also be used as mixtures, e.g. mixtures of polyethers and polyesters.

In some cases, it is particularly advantageous to use a combination of low melting and high melting polyhydroxyl compounds (German Offenlegungsschrift No. 2,706,297).

Compounds with a molecular weight of from 32 to 400 having at least two isocyanates reactive hydrogen atoms may also be used as starting components in preparing the polyurethane resins of the invention. These are also compounds containing hydroxyl groups and/or amino groups and/or thiol groups and/or carboxyl groups, and preferably hydroxyl groups and/or amino groups. They serve as chain lengthening agents or cross-linking agents. They generally have from 2 to 8, preferably 2 to 4 isocyanate reactive hydrogen atoms. These compounds with a molecular weight of from 32 to 400 and containing at least two isocyanate reactive hydrogen atoms may also be used as mixtures of such compounds. The following are examples of such compounds: ethylene glycol, propylene glycol-(1,2) and -(1,3), butylene glycol-(1,4) and -(2,3), pentanediol-(1,5), hexanediol-(1,6), octanediol-(1,8), neopentyl glycol, 1,4-bis-hydroxymethylcyclohexane, 2-methyl-1,3-propanediol, dibromobutenediol (U.S. Pat. No. 3,723,392), glycerol, trimethylol propane, hexanetriol-(1,2,6), trimethylolethane, pentaerythritol, quinitol, mannitol and sorbitol, castor oil, diethylene glycol, triethylene glycol, tetraethylene glycol, higher polyethylene glycols with a molecular weight of up to 400, dipropylene glycol, higher polypropylene glycols with a molecular weight of up to 400, dibutylene glycol, higher polybutylene glycols with a molecular weight of up to 400, 4,4'-dihydroxy-diphenylpropane, dihydroxymethylhydroquinone, ethanolamine, diethanolamine, N-methyldiethanolamine, triethanolamine and 3-aminopropanol.

Solutions of polyisocyanate polyaddition products, in particular of polyhydrazodicarbonamides and/or polyurethaneureas containing ionic groups, in low molecular, polyhydric alcohols may be used as polyol components according to the invention (German Offenlegungsschrift No. 2,638,759).

Suitable aliphatic diamines for the purpose of the invention include, for example ethylenediamine, 1,4-tetramethylenediamine, 1,11-undecamethylenediamine, 1,12-dodecamethylenediamine and mixtures thereof, 1-amino-3,3,5-trimethyl-5-aminomethylcyclohexane ("isophorone diamine"), 2,4- and 2,6-hexahydrotolylenediamine and mixtures thereof, perhydro-2,4'- and 4,4'-diaminodiphenylmethane, p-xylylene diamine, bis-(3-aminopropyl)-methylamine, diamino-perhydroanthracene (German Offenlegungsschrift No. 2,638,731) and cycloaliphatic triamines according to German Offenlegungsschrift No. 2,614,244. Hydrazine and substituted hydrazines, e.g. methyl hydrazine, N,N'-dimethylhydrazine and their homologues and acid dihydrazides may also be used according to the invention, e.g. carbodihydrazide, oxalic acid dianhydrides, the dihydrazides of malonic acid, succinic acid, glutaric acid, adipic acid, $\beta$-methyl-adipic acid, sebacic acid, hydracrylic acid and terephthalic acid; semicarbazidoalkylene hydrazides, e.g. $\beta$-semicarbazidopropionic acid hydrazide (German Offenlegungsschrift No. 1,770,591); semicarbazidoalkylene carbazic esters, e.g. 2-semicarbazidoethylcarbazic ester (German Offenlegungsschrift No. 1,918,504) or aminosemicarbazide compounds, e.g. $\beta$-aminoethylsemicarbazidocarbonate (German Offenlegungsschrift No. 1,902,931). The amino groups may be partly or completely blocked by aldimine or ketimine groups to control their reactivity (U.S. Pat. No. 3,734,894; German Offenlegungsschrift No. 2,637,115).

The following are examples of suitable aromatic diamines: bisanthranilic acid esters as described in German Offenlegungsschrift Nos. 2,040,644 and 2,160,590; 3,5- and 2,4-diaminobenzoic acid esters as described in German Offenlegungsschrift No. 2,025,900; diamines containing ester groups as described in German Offenlegungsschriften Nos. 1,803,635 (U.S. Pat. Nos. 3,681,290 and 3,736,350); 2,040,650 and 2,160,589; diamines with ether groups as described in German Offenlegungsschriften Nos. 1,770,525 and 1,809,172 (U.S. Pat. Nos. 3,654,364 and 3,736,295); 2-halogen-1,3-phenylenediamines optionally substituted in the 5-position (German Offenlegungsschriften Nos. 2,001,772; 2,025,896 and 2,065,869); 3,3'-dichloro-4,4'-diaminodiphenylmethane; tolylenediamine; 4,4'-diaminodiphenylmethane; 4,4'-diaminodiphenyldisulphides (German Offenlegungsschrift No. 2,404,976); diaminodiphenyldithioethers (German Offenlegungsschrift No. 2,509,404); aromatic diamines substituted with alkyl thio groups (German Offenlegungsschrift No. 2,638,760); diaminobenzenephosphonic acid esters (German Offenlegungsschrift No. 2,459,491); aromatic diamines containing sulphonate or carboxylate groups (German Offenlegungsschrift No. 2,720,166) and the high melting diamines described in German Offenlegungsschrift No. 2,635,400. The aminoalkyl thioanilines as described in German Offenlegungsschrift No. 2,734,574 are examples of suitable aliphatic-aromatic diamines.

The chain lengthening agents used according to the invention may also be compounds such as 1-mercapto-3-aminopropane, substituted or unsubstituted amino acids, e.g. glycine, alanine, valine, serine and lysine, and substituted or unsubstituted dicarboxylic acids, e.g. succinic acid, adipic acid, phthalic acid, 4-hydroxyphthalic acid or 4-aminophthalic acid.

Compounds which are nonfunctional in their reaction with isocyanates may also be used in proportions of from 0.01 to 10% by weight, based on the polyurethane solid content, to act as so-called chain breakers. Monofunctional compounds of this type include, for example, monoamines such as butylamine and dibutylamine, octylamine, stearylamine, N-methylstearylamine, pyrrolidine, piperidine and cyclohexylamine, monohydric alcohols such as butanol, 2-ethylhexanol, octanol and dodecanol, the various amyl alcohols, cyclohexanol and ethylene glycol monoethyl ether.

Water and/or readily volatile inorganic or organic substances may be used as blowing agents. Suitable organic blowing agents include e.g. acetone, ethyl acetate, halogenated alkanes such as methylene chloride, chloroform, ethylidene chloride, vinylidene chloride, monofluorotrichloromethane, chlorodifluoromethane and dichlorodifluoromethane; butane, hexane, heptane or diethylether. Air, carbon dioxide and nitrous oxide are examples of inorganic blowing agents. The effect of a blowing agent may also be obtained by the addition of compounds which decompose at temperatures above room temperature to liberate gases, for example compounds which liberate nitrogen, e.g. azo compounds such as azodicarbonamide or azoisobutyric acid nitrile. Other examples of blowing agents and details concerning the use of blowing agents may be found in Kunststoff-Handbuch, Volume VII, published by Vieweg and Höchtlen, Carl-Hanser-Verlag, Munich 1966, e.g. on pages 108 and 109, 453-455 and 507-510.

Known polyurethane catalysts may also be used. Examples include, e.g tertiary amines such as triethylamine, tributylamine, N-methyl-morpholine, N-ethyl-morpholine, N,N,N',N'-tetramethyl-ethylene diamine, pentamethyl-diethylene triamine and higher homologues (German Offenlegungsschriften Nos. 2,624,527 and 2,624,528); 1,4-diazabicyclo-(2,2,2)-octane; N-methyl-N'-dimethylaminoethyl-piperazine; bis-(dimethylaminoalkyl)-piperazines (German Offenlegungsschrift No. 2,636,787); N,N-dimethylbenzylamine; N,N-dimethylcyclohexylamine; N,N-diethyl-benzylamine; bis-(N,N-diethylaminoethyl)-adipate; N,N,N',N'-tetramethyl-1,3-butanediamine; N,N-dimethyl-$\beta$-phenylethylamine; 1,2-dimethylimidazole; 2-methylimidazole; monocyclic and bicyclic amidines (German Offenlegungsschrift No. 1,720,633); bis-(dialkylamino)-alkylethers (U.S. Pat. No. 3,330,782, German Auslegeschrift No. 1,030,558 and German Offenlegungsschriften Nos. 1,804,631 and 2,618,280); tertiary amines containing amide groups (preferably formamide groups) as described in German Offenlegungsschriften Nos. 2,523,633 and 2,732,292. Mannich bases of secondary amines such as dimethylamine and aldehydes, particularly formaldehyde, or ketones such as acetone, methyl ethyl ketone or cyclohexanone and phenols such as phenol, nonylphenol or bisphenol may also be used as catalysts.

The following are examples of tertiary amines with isocyanate reactive hydrogen atoms which may be used as catalysts: triethanolamine, triisopropanolamine, N-methyldiethanolamine, N-ethyl-diethanolamine, N,N-dimethylethanolamine and their reaction products with alkylene oxide such as propylene oxide and/or ethylene oxide and secondary-tertiary amines as described in German Offenlegungsschrift No. 2,732,292.

Silaamines with carbon-silicon bonds as described, e.g. in German Pat. No. 1,229,290 (corresponding to U.S. Pat. No. 3,620,984) may also be used as catalysts, e.g. 2,2,4-trimethyl-2-silamorpholine and 1,3-diethylaminomethyl-tetramethyl-disiloxane.

Basic nitrogen compounds such as tetraalkylammonium hydroxides, alkali metal hydroxides such as sodium hydroxide, alkali metal phenolates such as sodium phenolate and alkali metal alcoholates such as sodium methylate may also be used as catalysts. Hexahydrotriazines are also suitable catalysts (German Offenlegungsschrift No. 1,769,043).

The reaction between isocyanate groups and Zerewitinoff active hydrogen atoms can also be accelerated by lactams and azalactams which initially cause the formation of an associate between the lactam and the compound which has an acidic hydrogen. Such associates and their catalytic action have been described in German Offenlegungsschriften Nos. 2,062,288; 2,062,289 and 2,117,576 (U.S. Pat. No. 3,758,444); 2,129,198; 2,330,175 and 2,330,211.

Organometallic compounds may also be used as catalysts according to the invention, in particular organic tin compounds. The organic tin compounds used may be compounds containing sulphur, such as di-n-octyl tin-mercaptide (German Auslegeschrift No. 1,769,367; U.S. Pat. No. 3,645,927), tin(II) salts of carboxylic acids, such as tin(II) acetate, tin(II) octoate, tin(II) ethylhexoate or tin(II) laurate and tin(IV) compounds such as dibutyl tin oxide, dibutyl tin dichloride, dibutyl tin diacetate, dibutyl tin dilaurate, dibutyl tin maleate or dioctyl tin diacetate.

All the catalysts mentioned above may of course be used as mixtures. It is particularly preferred to use combinations of organic metal compounds and amidines, aminopyridines, or hydrazinopyridines (German Offenlegungsschriften Nos. 2,434,185; 2,601,082 and 2,603,834).

Other representatives of catalysts which may be used according to the invention and details concerning the activity of these catalysts may be found in Kunststoff-Handbuch, Volume VII, published by Vieweg and Höchtlen, Carl-Hanser-Verlag, Munich 1966, e.g. on pages 96 to 102.

The catalysts are generally used in a quantity of between about 0.001 and 10% by weight, based on the total quantity of compounds which have at least two isocyanate-reactive hydrogen atoms.

Surface active additives such as emulsifiers and foam stabilizers may also be used. Suitable emulsifiers include e.g. the sodium salts of ricinoleic sulphonate or salts of fatty acids with amines such as oleic acid diethylamine or stearic acid diethanolamine. Alkali metal or ammonium salts of sulphonic acids such as dodecylbenzenesulphonic acid or dinaphthylmethane disulphonic acid or of fatty acids such as ricinoleic acid or of polymeric fatty acids may also be used as surface active additives.

Suitable foam stabilizers are particularly the polyether siloxanes, and especially those which are water-soluble. These compounds generally have a polydimethyl siloxane group attached to a copolymer of ethylene oxide and propylene oxide. Foam stabilizers of this kind have been described, for example, in U.S. Pat. Nos. 2,834,748; 2,917,480 and 3,629,308. Polysiloxane polyoxyalkylene copolymers branched via allophanate groups as described in German Offenlegungsschrift No. 2,558,523 are in many cases particularly interesting.

Reaction retarders, e.g. substances which are acid in reaction such as hydrochloric acid or organic acid halides; known cell regulators such as paraffins or fatty alcohols or dimethyl polysiloxanes; pigments; dyes; flame retarding agents such as trischloroethylphosphate, tricresyl phosphate or ammonium phosphate and polyphosphate; stabilizers against ageing and weathering; plasticizers; fungistatic and bacteriostatic substances; and fillers such as barium sulphate, kieselguhr, carbon black or whiting may also be used.

Other examples of surface active additives, foam stabilizers, cell regulators, reaction retarders, stabilizers, flame retarding substances, plasticizers, dyes, fillers and fungistatic and bacteriostatic substances which may be used according to the invention and details concerning the use and mode of action of these additives may be found in Kunststoff-Handbuch, Volume VII, published by Vieweg and Höchtlen, Carl-Hander-Verlag, Munich 1966, e.g. on pages 103 to 113.

According to the invention, the components are reacted together by the known one-shot process, prepolymer process or semiprepolymer process, often using mechanical devices such as those described in U.S. Pat. No. 2,764,565. Details concerning processing apparatus which may also be used according to the invention may be found in Kunststoff-Handbuch, Volume VII, published by Vieweg and Höchtlen, Carl-Hanser-Verlag, Munich 1966, e.g. on pages 121 to 205.

According to the invention, the reaction for producing foam products may be carried out inside molds. In this process, the foamable reaction mixture is introduced into a mold which may be made of a metal such as aluminum or an artificial material such as epoxide resin, and it foams up inside the mold to produce the shaped product. This process of foaming in molds may be carried out to produce a product having a cellular structure on its surface or it may be carried out to produce a product having a compact skin and cellular core. According to the invention, the desired result can be obtained by either introducing just sufficient foamable reaction mixture to fill the mold with foam or introducing a larger quantity of reaction mixture than is necessary to fill the mold with foam. The second method is known as "over-charging", a procedure which has already been disclosed, e.g. in U.S. Pat. Nos. 3,178,490 and 3,182,104.

So-called external mold release agents such as silicone oils, are frequently used when foaming is carried out inside molds but the process may also be carried out with the aid of internal mold release agents, if desired in combination with external mold release agents, e.g. as disclosed in German Offenlegungsschriften Nos. 2,121,670 and 2,307,589.

Cold setting foams may also be produced according to the invention (see British Pat. No. 1,162,517 and German Offenlegungsschrift No. 2,153,086). Foams may, of course, also be produced by the process of block foaming or by the laminator process known per se.

When the polyhydroxyl compounds which may be obtained according to the invention after hydrogenation of the aldo and keto functions, without the use of other isocyanate reactive components, are reacted with highly elasticizing polyisocyanates, e.g. polyisocyanates with a biuret structure (German Auslegeschrift No. 1,543,178), hard lightfast, scratch-resistant and solvent resistant coatings and lacquers are obtained.

Polyether alcohols of high functionality can be obtained by propoxylation and/or ethoxylation of the sugar derivative of the invention and their hydrogenation products. Among these polyether alcohols, those with high hydroxyl numbers may be used for the production of rigid or semi-rigid cellular polyurethanes and those with low hydroxyl numbers as starting materials for highly elastic polyurethane foams.

Highly branched polyesters which may be used as additives to alkyd resins to improve their hardness are obtained by reaction of the products produced according to the invention and their hydrogenation products with carboxylic acids of the type mentioned above, e.g. phthalic acid, isophthalic acid, terephthalic acid, tetra- and hexahydrophthalic acid, adipic acid or maleic acid by the usual methods of polyester condensation, for example as described in Houben-Weyl, Methoden der organischen Chemie, Volume XIV/12, page 40. In particular the polyesters with hydroxyl groups, which are preferentially synthesized from the hydrogenated sugars according to the invention, may be used as starting components for the production of polyurethanes.

The products produced by the process according to the invention and their hydrogenation products readily react with long chain aliphatic monocarboxylic acids such as caprylic, capric, lauric, myristic, palmitic, stearic, oleic, linoleic, arachidonic and behenic acid and their derivatives, e.g. the methyl or ethyl esters or the anhydrides or mixed anhydrides to form esters containing hydroxyl groups. These esters, as also the ethoxylation products or the carbamic acid esters obtained by reacting the branched sugars according to the invention and their hydrogenation products with long chain monoisocyanates such as n-octyl, n-decyl, n-dodecyl, myristyl, cetyl or stearyl isocyanate (see e.g. K. Lindner, Tenside Vol. III, Wissenschaftliche Verlagsgesellschaft Stuttgart, 1964, page 2336) are nonionogenic, surface active compounds which are valuable emulsifiers, wetting agents and plasticizers.

The branched chain sugars according to the invention and their hydrogenation products may also be used as moisturizers in cosmetics and synthetic materials but they may also be used for other purposes, e.g. as antifreezes.

Their use as carbohydrate-containing substrates in the nutrient media of microorganisms is also a possibility. For this purpose, particularly suitable are those products of the process which consist mainly of branched monosaccharides containing from 5 to 9 carbon atoms (branched aldose and ketose sugars).

The following Examples serve to explain the process according to the invention. The numbers are parts by weight or percentages by weight unless otherwise indicated.

EXAMPLES

Example 1

This Example illustrates the conversion of D-glucose into a hitherto unknown branched chain $C_7$ sugar containing two primary hydroxyl groups and one tertiary hydroxyl group.

Variation A

1188 Parts of glucose.$H_2O$ (6 mole of dextrose hydrate) are dissolved in 1812 parts of water at 40° C. 710 Parts (7.1 mol) of a 30% aqueous formaldehyde solution (hereinafter termed "formalin solution") are then added all at once. The clear solution is heated to 80° C. with vigorous stirring. 36 Parts of N,N-dimethyl-cyclohexylamine (0.283 mol) are then added. The pH of the solution is 9.5. The pH falls to 7.8 in 40 minutes. Analytical determination of the free formaldehyde content shows that 79.3% by weight of the D-glucose have been α-C-methylated at the end of these 40 minutes. Stirring is then continued for a further 40 minutes at 84° C. until the free formaldehyde content of the solution has fallen to 0.87% and a pH of 6.4 has been reached. α-C-methlolation is by then completed to the extent of 94% of the theoretical yield. The solution obtained is only slightly yellowish in color. It is clarified with 10 parts of active charcoal. After removal of water at 15 Torr in a rotary evaporator, 1419 parts of a branched chain $C_7$ raw sugar containing 7.6% by weight of water and still containing about 3.46% by weight of dimethylcyclohexyl ammonium formate are obtained. This raw sugar has a viscosity of only 4873 mPas at 70° C. (while D-glucose is still crystalline at this temperature and does not melt even in the form of glucose monohydrate) (water content about 9.2% by weight). The α-methylolated, branched $C_7$ sugar is freed from catalyst and formic acid by desalting on an acid and then a basic ion exchange resin.

Carbonyl equivalent found: 0.45, calculated on the basis of the anhydrous reaction product.

The branched sugar shows no tendency to crystallization at a water content of 7.6%. Its optical activity $[\alpha_D] = +31°$.

The product, which has not been desalted and contains 7.5% of water, is acetylated with excess acetic anhydric and 1% by weight of sodium acetate as catalyst at 70° C. by introducing the product dropwise over a period of 2 hours into the acetic acid anhydride mixture from a dropping funnel which is heated to 70° C. As the degree of acetylation increases, the reaction product dissolves exothermically. Acetic acid and excess acetic acid anhydride are then removed, first at 15 Torr and then at 0.2 Torr at a reaction temperature of 50° C. The resulting hexaacetate of the $C_7$ sugar is soluble in chloroform as well as in toluene and in acetone. When the liquid reaction product is taken up in an equal quantity by weight of acetone, the sodium acetate precipitates. Acetone is distilled off under vacuum. The water insoluble sugar syrup is digested four times, each time with 500 parts of water, to remove small quantities of acetic acid. A hexaacetate of α-C-methylolated glucose which crystallizes extremely well and melts of 89° C. is thereby obtained.

Found molecular weight in toluene: 469 Calculated molecuolar weight: 462

Phenylhydrazone of the $C_7$ sugar: m.p. 198° C.

Variation B (preferred)

The procedure is the same as described for variation A and dimethylcyclohexylamine is again used as catalyst but the catalyst is added dropwise to the mixture in the reaction vessel over a period of two hours at such a rate that the pH of the solution remains constant within a range of about 8.3 to 8.4. The α-methylolated glucose is thereby obtained in a yield of 96% and maximum purity. It is of excellent color quality, and it has a carbonyl equivalent of 0.46, based on the anhydrous end product.

M.p. of the hexaacetate: 89° C.; soluble in chloroform and toluene.

Variation C (preferred for high solids cotents)

The procedure is as described for variation B but without the additional water as diluent. 594 parts (3 mol) of crystalline glucose hydrate are dissolved at 55° C. in 360 parts of 30% formalin solution (3.6 mol), i.e., a substantially higher concentration of reactants is employed (approximately 68%, if one takes into account the water introduced with the glucose hydrate). The reaction temperature is then raised to 78°–80° C. and the exothermic α-addition reaction is started by uniformly adding the dimethylcyclohexylamine to maintain the pH at 8.4–8.3, if necessary with slight cooling. By using a 30% by weight NaOH solution instead of the dimethylcyclohexylamine the same result is obtained. In this variation of the process, α-addition to α-methylolated glucose is completed within barely an hour with a final formaldehyde content in the solution of about 0.83%. The approximately 69.3% solution of α-C-methylolated glucose obtained is only pale yellow in color.

Carbonyl equivalent of the desalted end product: 0.455, based on the anhydrous product.

Yield: 678 parts (water content 9.2% by weight).

The viscosity of a 68% aqueous solution at 20° C. is only 339 mPas.

The viscosity of the sugar syrup concentrated to a water content of 9.2% is 8799 mPas at 50° C.

$\eta 60°$ C. = 2905 mPas $\eta 70°$ C. = 1170 mPas.

Example 2

The procedure is the same as described for variation B in Example 1, but only 6 mol of formaldehyde are used and the reaction is stopped at a concentration of 0.8% by weight. After acetylation of the end product, a mixture consisting of about 5 mol of the hexaacetylated α-aldolized glucose and 1 mol of pentaacetyl glucose is obtained.

M.p. of mixture: 81° C.

The non-acetylated product of the process has the advantage of being liquid so that it can more easily be propoxylated, ethoxylated or reacted with epichlorohydrin or with acetic anhydride. Even after 6 months' storage, D-glucose does not crystallize from the product.

Example 3

The procedure is exactly the same as described for variation B in Example 1 but the 460 parts of water are replaced by 460 parts of ethylene glycol. After elimination of the water in a thin layer evaporator at 16 Torr, a very low viscosity solution of the end product is obtained. The mixture contains about 26.6% by weight of ethylene glycol and has a viscosity of only 3800 mPas at 25° C.

Example 4

The procedure is as described for variation C in Example 1, using 0.33 mol of 30% NaOH as catalyst, but 37 mol of formaldehyde in the form of a 37% formalin solution (3000 parts) are used for the reaction instead of 7 mol of formaldehyde.

The fall in formaldehyde content is followed by titration. About 6 mol of formaldehyde have been used up after 3 hours. The solution obtained is then concentrated by evaporation in a thin layer evaporator at 0.4 Torr, and the idealized polyhemiacetal of the $C_7$ sugar is obtained:

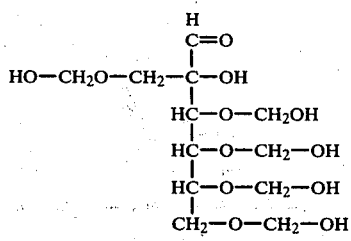

Yield: 2350 g (with a water content of 8% by weight); Average molecular weight: 360.

Model experiments show that the tertiary hydroxyl group on the $C_2$ atom does not undergo hemiacetal formation under the given conditions.

EXAMPLE 5

The procedure is the same as for variation B in Example 1 but the source of formaldehyde used is a formaldehyde synthesis gas obtained from the large scale production of formaldehyde, having substantially the following composition:

| | Nm³/h | Vol. % |
|---|---|---|
| $N_2$ | 6.73 | 31.607 |
| $H_2$ | 1.35 | 6.441 |
| $CO_2$ | 0.31 | 1.477 |
| CO | 0.02 | 0.099 |
| $\overset{O}{\underset{\parallel}{HC}}$—$OCH_3$ | 0.01 | 0.066 |
| $CH_4$ | 0.01 | 0.066 |
| $CH_2O$ | 3.83 | 17.565 |
| $H_2O$ | 8.93 | 42.012 |
| $CH_3OH$ | 0.14 | 0.667 |
| | 21.33 Nm³/h | 100.000 Vol. % |

The reaction with the synthesis gas is carried out intermittently at 80°–85° C. as follows: 426 liters per hour of synthesis gas containing approximately 102 g of formaldehyde are introduced for 2.1 hours into 6 mol of the aqueous glucose solution of Example 1 with stirring (total quantity of formaldehyde absorbed: ca. 210 g=7 mol). The process gases are introduced into the absorption liquid through an inlet pipe which opens into a cylindrical reaction vessel 0.5 cm above the bottom. Although the absorption liquid is not pumped in countercurrent to the process gas and no filling bodies are provided, i.e., the conditions provided by the apparatus are less advantageous than in the continuous process, approximately 98% of the formaldehyde is absorbed from the process gas and converted into α-C-methylolated glucose.

Carbonyl equivalent of the resulting α-C-methylolated glucose: 0.465.

EXAMPLE 6

The procedure is as described for variation B in Example 1 but different basic organic or inorganic catalysts are used in identical molar quantities:

(a) 0.28 mol of an aqueous 30% trimethylamine solution (b) 0.28 mol of an aqueous 50% triethylamine solution (c) 0.28 mol of an aqueous 50% endoethylenepiperazine solution (d) 0.28 mol of a 50% aqueous solution of the bicyclic amidine corresponding to the following formula

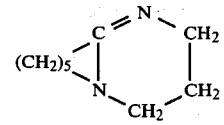

(e) 0.28 mol of choline [$(CH_3)_3N$—$CH_2$—$CH_2OH$]-$^\oplus OH^\ominus$ in an about 8% methanolic solution (f) 0.28 mol of a 30% NaOH solution (g) 0.28 mol of sodium cyanide (h) 0.28 mol of potassium cyanide.

The branched chain $C_7$ sugars are worked up and purified as described in Example 1.

The following carbonyl equivalents, based on 100 g of anhydrous end product, are found in experiments (a) to (h):

(a) Carbonyl equivalent: 0.45
(b) Carbonyl equivalent: 0.44
(c) Carbonyl equivalent: 0.45
(d) Carbonyl equivalent: 0.46
(e) Carbonyl equivalent: 0.46
(f) Carbonyl equivalent: 0.45
(g) Carbonyl equivalent: 0.468
(h) Carbonyl equivalent: 0.466

The theoretical carbonyl equivalent of α-methylolated D-glucose is 0.476.

In all samples, complete acetylation according to Example 1 results in an approximately 96% yield of an excellently crystallizing new hexaacetyl derivative which melts at 89° C. Reaction with phenyl hydrazine does not produce an osazone but the well crystallizing yellow hydrazone melting at 198° C. which corresponds to the following constitutional formula:

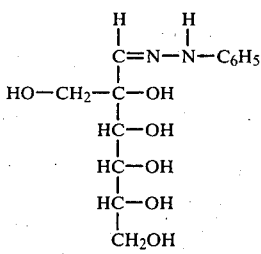

The fact that the C₇ sugars according to the invention do not form osazones with phenylhydrazine is proof of the α-addition of formaldehyde on the 2-C-atom of glucose.

EXAMPLE 7

The procedure is as described for variation B in Example 1 but the following catalysts are used:

(a) 0.14 mol

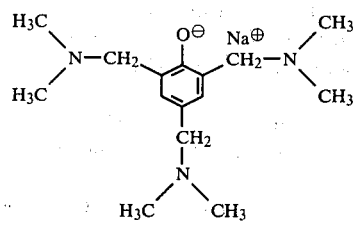

(b) 0.14 mol

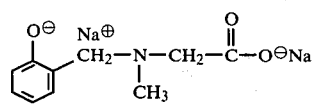

(c) 0.14 mol

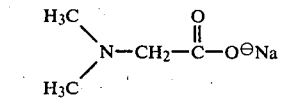

(d) 0.14 mol

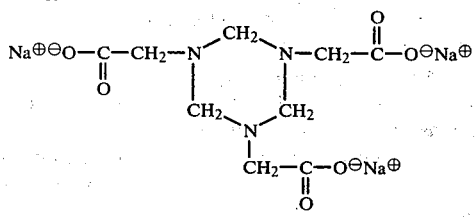

The following carbonyl equivalents, based on 100 g of anhydrous end product, are found in experiments (a) to (d):

(a) carbonyl equivalent: 0.45
(b) carbonyl equivalent: 0.46
(c) carbonyl equivalent: 0.45
(d) carbonyl equivalent: 0.46

Example 8

The procedure is the same as in variation B in Example 1 but the α-addition reaction of formaldehyde to D-glucose is carried out with 30% of sodium hydroxide solution as catalyst and at a pH of approximately 7.5 instead of 8.4–8.5. Reaction temperature: 82° C.

The reaction time of α-addition at pH=7.5 until the residual formaldehyde content has fallen to 0.8% is 11 hours, 40 minutes.

The product is worked up as described in Example 1. The carbonyl equivalent, based on 100 g of anhydrous end product, is 0.46.

The reduction in the pH by about 1 unit thus slows down the reaction time by a factor of 8 compared with the reaction carried out at the preferred pH of 8.4–8.5.

Example 9

The procedure is the same as described for variation C in Example 1 but the size of the batch is reduced and only 2 mol of D-glucose and 120 parts of a 60% aqueous formaldehyde solution (2.4 mol of formaldehyde) preheated to 70° C. are used. 12 parts of dimethylcyclohexylamine is used as catalyst.

An end product having an extremely high concentration of the C₇ sugar is obtained in this way. The crude product, with a water content of approximately 16.5% and still containing dimethylcyclohexylammonium formate has a viscosity of only 28,300 mPas at 25° C.

EXAMPLE 10

The procedure is the same as for variation B in Example 1 except that no formaldehyde is initially added to the glucose but the quantity of glucose in aqueous solution mentioned there is stirred up with 0.2 mol of pyridine at pH=7.8 or 0.2 mol of quinoline at pH=8.3 for one hour at 85° C., i.e., a Lobry de Bruyn or van Eckenstein rearrangement is carried out in accordance with the reaction scheme indicated below (see P. Karrer, Lehrbuch der Organischen chemi, 13th Edition, 1959, page 368):

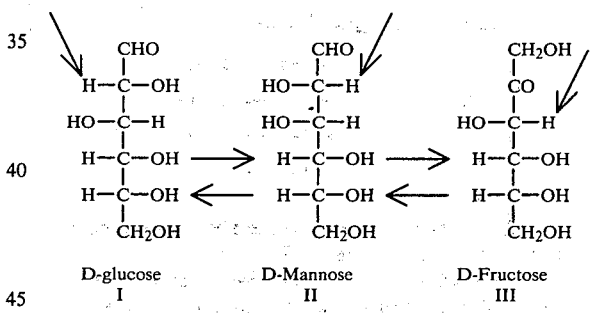

Equilibria between monosaccharides I, II and III are established under these conditions. α-Addition of formaldehyde is then carried out according to variation B of Example 1 at the points indicated by the arrows in formulae I, II and III, using dimethylcyclohexylamine as catalyst at pH=8.3. The carbonyl equivalent of the end product, based on the anhydrous C₇ sugar mixture, is 0.45.

An Amadori rearrangement, Heyns rearrangement or Maillard reaction may be carried out in the same way on mono- and disaccharides which reduce Fehling's solution, using amino acids or primary amines, and the C-methylolation with formaldehyde according to the invention may then be carried out in a second stage. This also results in new branched chain sugars which are capable of reacting with phenyl hydrazine to form only phenylhydrazone.

EXAMPLE 11

The procedure is the same as for variation B in Example 1 but using the following C₅ sugars:
(a) 15 parts of D-ribose (0.1 mol)

(b) 15 parts of D-xylose (0.1 mol)
(c) 15 parts of D-arabinose (0.1 mol)
and α-addition of formaldehyde is carried out on a 60 times smaller scale, compared with Example 1.

Carbonyl equivalent found per 100 g of anhydrous compound for (a): 0.55.
Carbonyl equivalent found per 100 g of anhydrous compound for (b): 0.54.
Carbonyl equivalent found per 100 g of anhydrous compound for (c): 0.55.
Calculated carbonyl equivalents per 100 g of anhydrous compound for (a), (b) and (c): 0.56.

EXAMPLE 12

The following Example illustrates how the process according to the invention may be carried out on natural and artificial invert sugars and on isosyrups of corn starch and potato starch hydrolysates, which are industrially particularly interesting due to their low cost and which consist mainly of 1 mol of glucose and 1 mol of fructose. The procedure is exactly as described for variation B in Example 1 and the following substances are used:

(a) 6 mol of a natural invert sugar (bees' honey) consisting substantially of D-glucose and D-fructose and having a water content of 19.1%, a viscosity of 11,848 mPas at 20° C. and a carbonyl equivalent of 0.55, based on 100 g of the anhydrous product.

(b) 6 mol of an "isosyrup" produced by enzymatic hydrolysis of corn starch and potato starch and having a water content of 15.2%, a viscosity at 25° C. of 26,169 mPas and a carbonyl equivalent of 0.53, based on 100 g of the anhydrous product.

(c) 6 mol of an artificial invert sugar which has been prepared from 3 mol of saccharose (cane sugar) by 7 hours' hydrolysis with a strongly acid ion exchange resin at 70° C. and which has a water content of 20%. Carbonyl equivalent based on 100 g of the anhydrous product: 0.5.

The method of carrying out the reaction and working up the end product is exactly the same as described in Example 1, i.e., only 7.1 mol of formaldehyde are used so that fructose also undergoes only C-monomethylolation.

Carbonyl equivalents found per 100 g of anhydrous end product:
(a) 0.43
(b) 0.44
(c) 0.41.

EXAMPLE 13

The procedure utilizes the sugar of variation (b) in Example 12, and 13 mol of formaldehyde are used for 6 mol of the mixture consisting substantially of D-glucose and D-fructose, so that the D-fructose component can be α,α'-C-methylolated three times over. The catalyst, reaction temperature, pH and working up are the same as in Example 1, variation (B).

A 20% aqueous solution of the α-aldolized glucose and a substantially threefold C-methylolated fructose has a viscosity at 25° C. of 24,800 mPas. The carbonyl equivalent found is 0.34, based on 100 g of anhydrous mixture.

Calculated carbonyl equivalent of 100 g of a mixture of 1 mol of methylolated D-glucose and 1 mol of trimethylolated D-fructose: 0.37.

On average, therefore, the D-glucose is in fact C-methylolated once and the D-fructose portion in the isosyrup is α-α'-methylolated approximately three times.

Acetylation of these $C_7$–$C_9$ sugar mixtures by the method described in Example 1 results in crystallized acetyl derivatives which are soluble in chloroform.

EXAMPLE 14

This example illustrates the process according to the invention applied to disaccharides which reduce Fehling's solution, in particular
(a) maltose, m.p.: 102.5° C.
(b) lactose, m.p.: 201.6° C.
(c) cellobiose, m.p.: 225° C.

The procedure is exactly as described for variation B, Example 1, but using only 17.1 parts of the disaccharide (0.05 mol) in each case and 3 parts of formaldehyde (0.1 mol) and 0.3 parts of dimethylcyclohexylamine as catalyst. Reaction temperature: 82° C., pH control: 8.3 to 8.5.

The found carbonyl equivalents of the α-C-methylolated disaccharides were as follows:
(a) 0.26
(b) 0.25
(c) 0.24

The calculated carbonyl equivalents for α-C-methylolated maltose, lactose and cellobiose are 0.27.

The products (a), (b) and (c) react virtually quantitatively with phenyl hydrazine to form hydrazones and no osazones. This was found to be due to the fact that the tertiary hydroxyl group on the 2-C-atom prevents osazone formation.

The trisaccharides ($C_{18}H_{32}O_{16}$), raffinose, which is concentrated in molasses, and gentianose and melecitose, the tetrasaccharide stachyose found in the seeds of many leguminous plants and the pentasaccharide verbascose do not reduce Fehling's solution and are only accessible to α-C-methylolation according to the invention if they are first completely or partly hydrolyzed, for example in a one-pot process, e.g. as described in Example 12, variation c, into galactose, glucose and fructose or fructose and gentiobiose, or glucose and fructose or galactose, glucose and fructose.

EXAMPLE 15

This example illustrates the α- or α,α'-C-methylolation of plant hydrolysates or hydrolysates of living masses such as baker's yeast, nutrient yeasts or brewer's yeast, i.e. types of yeast which bring about the alcoholic fermentation of D-glucose, D-fructose, etc.

(a) 165 Parts of moist, freshly cut grass (dry weight 32 parts) are hydrolyzed in an autoclave under pressure for 6 hours at 130° C. in the presence of 300 parts of water and 0.4 parts of sulphuric acid. Various storage polysaccharides, sugar-like cell contents, celluloses and hemicelluloses, proteins and nucleic acids containing ribose and deoxyribose are partially hydrolyzed in the process and converted into water-soluble mono- and oligosaccharides. After filtration, removal of sulphuric acid and acids derived from the plant material, such as phosphoric acids, by a commercial basic ion exchange resin and concentration by evaporation under vacuum, a syrupy liquid is obtained. The hydrolyzed amino acids present in it react with the keto and aldehyde functions of the hydrolyzed polysaccharides in the course of the process of evaporation to form yellowish brown products by Maillard reactions. Yield: 17 parts, carbonyl equivalent: 0.38.

(b) The procedure is exactly as described under (a) but using a moist, undried bakers' yeast (150 parts). Yield: 19 parts of a brown syrup, carbonyl equivalent: 0.41.

The syrupy mixtures obtained according to (a) and (b) contain a wide spectrum of monosaccharides and oligosaccharides.

The sugar mixtures in the amount obtained by (a) and (b) are methylolated by the method described for variation B in Example 1, using 20 parts of a 30% formalin solution (0.2 mol of formaldehyde). 1.06 Parts of dimethylcyclohexylamine are used as catalyst and C-methylolation is carried out for 80 minutes at 85° C.

Carbon equivalent found in (a), based on 100 g of anhydrous product: 0.33. Carbonyl equivalent found in (b), based on 100 g of anhydrous product: 0.35

Example 16

(Example for practical application)

This example illustrates that extreme reductions in viscosity can be achieved simply by mixing the new $C_7$ sugars with aminoplast formers such as N-methylolcaprolactam, $\epsilon$-caprolactam, urea, thiourea, dicyandiamine, and the like, phenoplast formers, such as phenol or dimethylphosphite or diethylphosphite. The mixtures may therefore be reacted even at room temperature with various reactants, including also polyisocyanates, for example.

(a) A mixture of 1 mol of $\alpha$-C-methylolated D-glucose from Example 1, variation B and 2 mol of N-methylolcaprolactam has a viscosity at 35° C. of only 4800 mPas.

(b) A mixture of the exceptionally low cost $\alpha$-C-methylolated isosyrup from Example 13 and 2 mol of $\epsilon$-caprolactam has a viscosity at 35° C. of only 17,800 mPas.

(c) A mixture of 1 mol of $\alpha$-C-methylolated artificial invert sugar (prepared from saccharose according to Example 12 c) and 1.5 mol of urea has a viscosity at 35° C. of 14,500 mPas.

(d) $\alpha$-C-methylolated glucose, e.g. from Example 1, and the commercially particularly interesting $\alpha,\alpha'$-polymethylolated isosyrup from Examples 12 and 13 can be mixed in any proportions with dimethylphosphite, diethylphosphite and triethylphosphate to form extremely low viscosity solutions. They may also be esterified in various ways by ester interchange reactions accompanied by elimination of the alcohol component of the phosphites, simply by application of a vacuum at temperatures of only 40 to 50° C. Thus, a mixture of 1 mol of the methylolated sugar mixtures mentioned above (i) with 2 mol of dimethylphosphite has a viscosity at 25° C. of only 320 mPas and (ii) with 2 mol of diethylphosphite has a viscosity at 25° C. of only 450 mPas.

EXAMPLE 17

Use of $\alpha$-methylolated isosyrups prepared according to the invention and their modification products for the production of rigid foams:

A mixture of
100 parts of the end product of Example 12 (b) which has been hydrogenated with 6 parts of Raney nickel at a hydrogen pressure of 80 bar, a temperature of 100° C. and a pH-value of 12, and subsequently reacted with sodium hydroxide and propylene oxide to form a polyether with hydroxyl number 480,
1.5 parts of a commercial silicone stabilizer (stabilizer OS 610 of Bayer AG),
0.5 parts of endoethylenepiperazine,
4.5 parts of a liquid associate mixture of 2.5 parts of $\epsilon$-caprolactam and 2 parts by weight of water and
40 parts of monofluorotrichloromethane is vigorously mixed with 152 parts of a commercial phosgenation product of an aniline formaldehyde condensate (isocyanate content 29%). The mixture rapidly and uniformly foams up. The resulting foam with closed cells has a density of 38 kg/m³.

If it is desired to produce substantially open celled, highly flame resistant rigid foams, the branched chain sugars of Examples 1 to 16 may be used to produce foams in analogous manner. Rigid foams with density of 30 to 24 kg/m³ are thereby obtained.

The high flame resistance of these rigid foams, in particularly those obtained from mixtures containing aminoplast monomers, is presumably due to the water of dehydration from the sugars and the water which in the event of fire is formed by condensation of carbonyl groups of the $\alpha$-methylolated sugars with the aminoplast monomers.

EXAMPLE 18

(a) 212 parts by weight of an aqueous, 50% strength solution of the glucose prepared in Example 1, variant A, desalted on ion exchange resins and methylolated on the $\alpha$-C atom are hydrogenated with 80 g Raney nickel in a 0.7 liter autoclave at 150 bars of hydrogen pressure for 4 hours at 30° C., then for 1 hour at 60° C. and finally for 1 hour at 100° C.

A slightly yellowish solution of a new polyalcohol containing 7 hydroxyl groups and having the following constitution

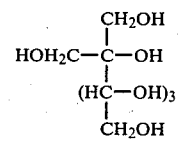

was obtained. The new branched polyalcohol has 3 primary reactive hydroxyl groups and is, for example in the case of isocyanate reactions, a considerably more reactive cross-linking agent than sorbitol. The new sugar does not readily crystallize completely. Whereas sorbitol melts at about 100° C. with one mole of crystallization water, the new polyalcohol according to the invention is with one mole of crystallization water (=about 5.6% by weight of $H_2O$) and at 50° C., of a honey-like viscosity and can already be mixed with other polyalcohols at 50° C. and can be used as a cross-linking agent for isocyante reactions or as a moisture-retaining agent, whereas this is not possible with sorbitol. Residual content of carbonyl groups 0.016%.

(b) Complete elimination of the residual content of carbonyl groups is possible according to the following method:

100 g of catalyst (Raney-Ni/Fe in the ratio 85:15), suspended in 1 liter water, are placed in a 3 liter stainless steel autoclave and heated to hydrogenation temperature (150° C.). The remaining volume is then filled with hydrogen gas up to a working pressure of 150 bars. 500 ml of a 50% aqueous solution of $\alpha$-C-methylolated glucose, prepared according to example 1, variant A are pumped into the autoclave in the course of 7 minutes.

Then 500 ml of the hydrogenated solution is discharged via an ascending pipe fitted with a frit, the latter holding back the catalyst, the next batch is pumped in and is hydrogenated in the same way as the first batch. The same procedure is followed with 5 further batches each of 500 ml. No loss of catalyst can be detected after this number of cycles. The hydrogenated $C_7$ polyalcohol solutions are collected, de-ionized via ion exchangers and freed from the main quantity of water in the thin layer evaporator. An only slightly yellowish-coloured $C_7$-polyalcohol with the following properties is obtained:

residual water content: 5.6% residual carbonyl content: none detected, OH-number: 1860.

The reaction product is a highly viscous, non-crystallizing branched $C_7$-polyalcohol easily mixable with ethylene glycol and able to be adjusted to OH functionalities of 6–2.5 by the addition of ethylene glycol.

(c) The same procedure is followed as that described under (b) and discontinuous hydrogenation is conducted with ruthenium as catalyst.

In a 3 liter autoclave 45 g of catalyst (5% ruthenium on carbon), suspended in 500 g water, are activated by hydrogenating at 125° C. and 200 bars of $H_2$ within 60 minutes. After cooling the suspension 1500 g of a 30% aqueous solution of a completely de-ionized branched $C_7$ sugar of example 1, variant A(pH=6) are added.

With a starting pressure of 150 bars of $H_2$ the mixture is heated for 30 minutes to the desired temperature of 125° C. Hydrogenation is continued for a further 90 to 120 minutes at 125° C. and 200 bars of $H_2$. As hydrogenation product a colourless solution of $C_7$ polyalcohols is obtained which, after filtering off the catalyst is concentrated in vacuo to form a syrup-like composition.

Yield: 500 parts by weight; containing 5.5% by weight of water.

Example 19

212 parts by weight of the branched $C_7$ polyalcohol according to Example 18 which is easily stirrable at 60° C., can be partially acetylated on the primary hydroxyl groups with 3 mols of acetic anhydride with the addition of 0.4 parts by weight of sodium acetate. A partially acetylated, branched polyalcohol, which is readily mixable with polyesters and polyethers and which has the idealised constitution:

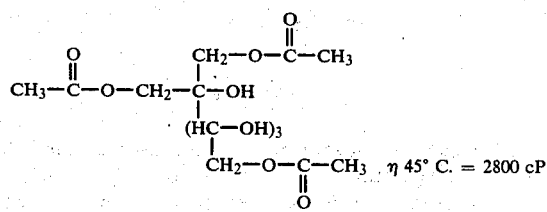

is obtained which transfers its elasticating properties when used as cross-linking agent in polyurethane hard foams and decreases the brittleness of highly cross-linked foams.

Example 20

(a) 224.6 parts by weight of the branched $C_7$ sugar prepared in example 1, variant A, having a water content of 6.5% by weight are mixed while stirring under a nitrogen atmosphere with 1.5 g each of a complex of 1 mole boron trifluoride and 1 mole acetic acid at room temperature. The starting batch is stirred well under a nitrogen atmosphere and 406 parts by weight (=7 moles) propylene oxide are added slowly and uniformly at 49° C. in the course of 2 hours. After adjusting the pH value to 7.2 using Sodium hydroxide solution or aqueous 25% ammonia solution the starting batch is freed in vacuo at 50° C., from traces of propylene oxide and small amounts of water. Branched polyethers are obtained with surprisingly low viscosity and a low proportion of groups having a reducing action.

Yield: 612 g; OH-number: 635; acid number 0.7; viscosity 1600 mPas/35° C.

The low content of only 3.1% of sugar having a reducing effect shows that in the propoxylation the carbonyl groups in the reaction products were, surprisingly, acetalised to a considerable extent. Over 90% of the aldehyde groups present in the branched $C_7$ sugar were therefore acetalised. The new, branched polyethers are more compatible with high-and low-molecular polyhydroxyl compounds, inded also with isocyanates than dehydrated starting polyalcohols. Further, it is particularly important that the branched polyethers obtained are considerably more active in their reaction with polyisocyanates than formose polyethers prepared usually by $OH^\ominus$ catalysis in the presence of sodium hydroxide solution or potassium hydroxide solution.

(c) If 224.6 parts by weight of the polyalcohol hydrogenated in example 18, variant b, are used and the same procedure is followed as that of (a) an almost colourless polyether is obtained in a yield of 616 g, which is completely free from dioxolane units and constituents having a reducing effect. OH number 650.

Example 21

2240 g of the polyhydric branched polyalcohol described in example 18, variant (b) and 600 g of toluene are placed in the reactor at room temperature. By evacuating the reaction vessel twice and filling it up again each time with nitrogen the atmospheric oxygen is removed. After heating to 80° C., 80 g of 50% aqueous potassium hydroxide solution are added. Afterwards the reaction mixture is heated further. At between 100°–115° C., 52.8 g water (solvent water and reaction water from the potassium hydroxide solution) are distilled off azeotropically. After the distillation is completed 6112 g of propylene oxide are gradually added (500 g/hour) to the very easily stirrable mixture at 100°–105° C. and at a pressure of 0.4 to 0.6 bars. The reaction temperature is kept within this range by either cooling or heating the reaction mixture, as required. After the addition of propylene oxide has been completed stirring is continued for a further three hours at 100°–105° C.

The alkaline polymer is neutralised with 284 g of 12.5% aqueous sulphuric acid after 800 g of water has been added (pH value of the emulsion: 6.8). Afterwards the water is distilled off in vacuo at 70° to 90° C. after adding filtration auxiliaries (cellulose powder and synthetic magnesium silicate) and an anti-oxidant (2.6 di-tert.-butyl-p-cresol). With a water content of 0.9% the deposited salts and the filtration auxiliaries are filtered off. In order to remove the water completely the filtrate is subsequently distilled in vacuo at 100°–105° C.

The almost colourless product obtained has the following physical data:

| | |
|---|---|
| hydroxyl number (mg KOH/g) | 300 |
| pH value | 7.6 |
| water content (%) | 0,05 |
| viscosity 25° C. (mPas) | 5440 |

The polyether polyol obtained in this way can be processed to form a hard polyurethane foam. Owing to the low viscosity of the polyether obtained the reaction mixture has improved flowability compared with commercially available sucrose polyethers.

Example 22

424 parts by weight of the almost colourless branched $C_7$ sugar obtained by NaCN-catalysis are already esterified at 60° C. with 1 mole of oxalic acid in a rapid esterification reaction and without any significant dehydration preferably at their primary hydroxyl groups with separation of 36 parts by weight of condensation water. A polyester of the following idealized constitution:

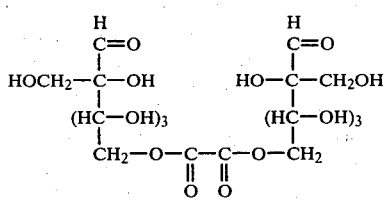

is obtained in a yield of 456 parts by weight and which can be dissolved in polyesters of adipic acid and diethylene glycol of an average molecular weight of 2000 to 30% by weight, whereas a comparable glucose oxalic acid condensate is not mixable in the same polyester.

Example 23

(a) 200 g of the branched polyhydric polyalcohol described in example 18, varian (b) are dehydrated in the thinlayer evaporator at 100° C. and 0.06 mmHg and reacted with 0.5 g triethylene diamine. The mixture is heated to 100° C. At this temperature 281 g of stearyl isocyanate are added dropwise within 40 minutes and the mixture is subsequently stirred until no more isocyanate is able to be detected with the aid of the IR spectrosopy. After cooling a wax-like product is obtained with good surface-active properties, which represents an excellent emulsifier of emulsifying water in polyisocyanates.

(b) 424 g of the branched, polyhydric polyalcohol (as in a) are dehydrated at 100° C. at 0.06 mmHg. The anhydrous mixture is reacted with 1600 g of dimethyl formamide and 562 g of stearic acid methyl ester. 70 g of a 30% sodium methylate solution are added to the mixture at room temperature and the mixture is subsequently stirred at 95°–100° C. and 180 mmHg until no more methanol is distilled off.

After distilling off the dimethyl formamide a waxlike composition is obtained which is freed from excess polyalcohol mixture by treating with hot water. The aqueous suspension is pressed free of excess water and dried in vacuo. A wax-like composition is obtained having good surface active properties, and representing a good emulsifier for emulsifying water and water-soluble polyalcohols in hydrophobic polyether.

Example 24

(a) According to the method of procedure of DE-OS (German Published Application) No. 2,031,160 and German DE-OS No. 1,953,347 (impregnation reactions) a hydrophilic polyurethane softfoam quadrate measuring 20 cm×10 cm×5 cm=1000 cm³ volume, which contains approximately 40% by weight of polyethylene oxide segments in its polyether part is impregnated with a 50% aqueous solution of a $C_7$-branched alcohol which was prepared according to example 1, variant A and subsequent hydrogenation; the foam spontaneously swelling considerably and uniformly within the dimensions of the volume. The increase in volume of the quadrate achieved is, after the impregnation agent has been squeezed out and after drying at 30° C. in vacuo, 2000 cm³, i.e. by means of impregnation and swelling an additional volume of approximately 30 parts by weight of branched hydrogenated $C_7$ sugars and approximately 12 parts by weight of water are fixed by the moisture-retaining agent used. The marked swelling of the foam is caused by solvation of the soft segments of the foam. The water is not lost at long storage periods of 2 months. The foam retains its considerably softer feel in contrast to the non-impregnated foam used. Films made from foams of this kind which have been increased in their volume by a swelling process with the moisture-retaining agents of the invention, have a very soft non-sticky feel and are particularly suitable for use as chloths for wiping car windscreens to prevent iceformation at freezing temperatures of approx. $-10°$ C.

(b) The same procedure is followed as in (a) and prior to impregnation.

(1) 20 parts by weight of commercially available Nivea cream are dispersed in the sugar solution of the invention (2) 20 parts by weight of commercially available shoecream are dispersed in the sugar solution according to the invention.

The additives mentioned under (1) and (2) do not even dry up after 3 months of storage in the open air (22°–25° C.).

Example 25

100 parts by weight of a sugar of the constitution:

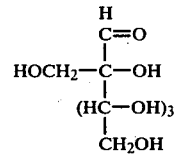

containing 6% by weight of water are dissolved in 900 g water. The starting material is reacted with 1 g ammonium carbonate, 1 g primary potassium phosphate and 100 g of moist baker's yeast (=20 g by weight of yeast). The suspension is stirred under an atmosphere of nitrogen. The yeast is at the stage of cell division, it multiplies and at the same time the enzymatic partial fermentation reaction begins. The $CO_2$ evolved is absorbed in a 1 N NaOH solution by passing a nitrogen stream over the stirred suspension, $CO_2$ is determined by the barium carbonate method and the fermentation curve (separation of $CO_2$ as a function of time) is graphically recorded.

After 4.5 hours the evolution of $CO_2$ is practically over and 18.5 g of $CO_2$ are released and 20.6 g of ethanol are produced.

The mathematical evolution leads to the result that half of the new branched $C_7$ sugar (=α-C-methylolated glucose) is enzymatically split off into the cover part of the molecule.

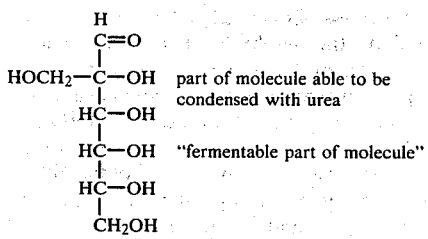

0.45 moles of the separated polyhydroxyaldehyde radical:

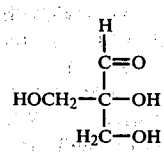

condense with 20 g of added urea (=0.33 moles) to form an organe-coloured syrup. (Yield: 71 g)

What is claimed is:

1. A derivative of a reducing sugar other than ribose, said reducing sugar having a molecular weight of from 120 to 2000, said derivative having at least one methylol group which branches the carbon structure of the reducing sugar in the α-position, the α'-position, or both the α- and α'-position to the carbonyl group or cyclohemiacetal group of the reducing sugar.

2. α-C-Methylolated glucose.
3. α-C-Methylolated arabinose.
4. α,α'-C-Trimethylolated fructose.
5. α-C-Methylolated maltose.
6. α-C-Methylolated lactose.
7. α-C-Methylolated cellobiose.
8. α,α'-C-Methylolated invert sugar.
9. A liquid mixture comprising
   (a) 95 to 5% by weight of a derivative of a reducing sugar other than ribose, said reducing sugar having a molecular weight of from 120 to 2000, said derivative having at least one methylol group which branches the carbon structure of the reducing sugar in the α-position, the α'-position or both the α- and α'-positions to the carbonyl group or cyclohemiacetal group of the reducing sugar; and
   (b) 5 to 95% by weight of a member selected from the group consisting of glucose, succharose, and mixtures thereof.

10. The mixture of claim 9 wherein said derivative is α-Methylolated glucose.
11. The mixture of claim 9 wherein said derivative is α-Methylolated arabinose.
12. The mixture of claim 9 wherein said derivative is α,α'-Trimethylolated fructose.
13. The mixture of claim 9 wherein said derivative is α-Methylolated maltose.
14. The mixture of claim 9 wherein said derivative is α-Methylolated lactose.
15. The mixture of claim 9 wherein said derivative is α-Methylolated cellobiose.
16. The mixture of claim 9 wherein said derivative is α,α'-Methylolated invert sugar.
17. A liquid mixture comprising
   (a) 99 to 5% by weight of a derivative of a reducing sugar other than ribose, said reducing sugar having the molecular weight of from 120 to 2000, said derivative having at least one methylol group which branches the carbon structure of the reducing sugar in the α-position, the α'-position or both the α- and α'-positions to the carbonyl group or cyclohemiacetal group of the reducing sugar; and
   (b) 1 to 95% by weight of a member selected from the group consisting of alkylphosphites, aminoplast monomers, phenoplast monomers, low molecular alehydes and ketones, which have at least one methylol group in the α-position to the carbonyl group, and mixtures thereof.

18. The mixture of claim 17 wherein said derivative is α-Methylolated glucose.
19. The mixture of claim 17 wherein said derivative is α-Methylolated arabinose.
20. The mixture of claim 17 wherein said derivative is α,α'-Trimethylolated fructose.
21. The mixture of claim 17 wherein said derivative is α-Methylolated maltose.
22. The mixture of claim 17 wherein said derivative is α-Methylolated lactose.
23. The mixture of claim 17 wherein said derivative is α-Methylolated cellobiose.
24. The mixture of claim 17 wherein said derivative is α,α'-Methylolated invert sugar.
25. A process for the preparation of sugar derivatives comprising reacting a reducing sugar, said reducing sugar having a molecular weight of from 120 to 2000, with from 0.05 to 10 mol of formaldehyde based on the equivalents of the hydrogen atoms in the α- and α'-position to the carbonyl group or cyclohemiacetal group of the reducing sugar, at a pH of from 7.4 to 11 and a temperature of from 40° to 110° C.
26. The process of claim 25 wherein the reaction is conducted in the presence of a material selected from the group containing water, monohydric or polyhydric alcohols having a molecular weight of from 32 to 10,000, and mixtures thereof.
27. The process of claim 25, wherein from 0.2 to 5 mol of formaldehyde, based on the quantity required for complete methylolation, is used.
28. The process of claim 25, wherein tertiary amines or quaternary ammonium bases are used to adjust the pH.
29. The process of claim 25, wherein cyanides of alkali metals are used to adjust the pH.
30. The process of claim 25, wherein the source of formaldehyde is selected from the group consisting of aqueous formalin solutions, alcoholic formalin solutions, paraformaldehyde dispersions, formaldehyde releasing compounds containing from 10 to 70% by weight of formaldehyde and mixtures thereof.
31. The process of claim 30, wherein N-methylol compounds of aminoplast monomers are used as source of formaldehyde.
32. The process of claim 25, wherein the source of formaldehyde used is a synthesis gas containing formaldehyde, which synthesis gas is passed through an aqueous and/or alcoholic solution of the reducing sugar to be methylolated, which solution may contain a member selected from the group consisting of alkylphosphites, aminoplast monomers, phenoplast monomers, additional low molecular aldehydes, ketones which are capable of α-methylolation and mixtures thereof.

33. The process of claim 32, wherein the synthesis gas is passed continuously through an absorption column in which the reducing sugar solution is pumped in countercurrent to the synthesis gas and the absorption liquid is continuously removed from the system at such a rate that the volume of absorption liquid in the absorption column remains substantially constant.

34. The process of claim 23, wherein the sugar solution contains no basic catalyst and the methylolation reaction is brought about by addition of an inorganic or organic base only after absorption of the formaldehyde.

35. The process of claim 33, wherein the methylolation reaction only partly takes place in the absorption column, the remainder of the reaction taking place in a following reaction vessel.

36. The process of claim 35, wherein the methylolation reaction which occurs outside the absorption column takes place in a cascade of stirrer vessels.

37. The process of claim 35, wherein the methylolation reaction which occurs outside the absorption column takes place continuously in a reaction tube.

38. The process of claim 33, wherein a member selected from the group consisting of inorganic base, organic base, and mixtures thereof, is introduced continuously into the absorption column at such a rate that its concentration in the absorption liquid is between 0.01 and 10% by weight so that absorption of formaldehyde and the methylolation reaction take place simultaneously in the absorption column.

39. The process of claim 25, wherein the reaction mixture contains from 10 to 60% by weight of monohydric or polyhydric alcohols having a molecular weight of from 32 to 10,000.

40. The process of claim 25, wherein the reaction mixture contains from 1 to 50% by weight of a member selected from the group consisting of aminoplast monomers, phenoplast monomers, low molecular weight aldehydes, ketones which are capable of being α-methylolated, and mixtures thereof.

41. The process of claim 25, wherein from 0.04 to 0.06 mol, based on the aldehyde or keto equivalent of the reducing sugar, of a member selected from the group consisting of organic bases, inorganic bases, and mixtures thereof, are present during the methylolation reaction.

42. The process of claim 25, wherein any residual formaldehyde content still present after the methylolation reaction is bound by the addition of a member selected from the group consisting of aminoplast forming monomers, phenoplast forming monomers, primary or secondary amines, alkylphosphites and mixtures thereof.

43. The process of claim 25, wherein any residual formaldehyde present in the reaction product is bound by acidification to pH values from 1 to 3, accompanied by intramolecular or intermolecular acetal formation.

44. The process of claim 25, wherein the carbonyl groups in the reaction product are converted into hydroxyl groups by subsequent catalytic reduction with hydrogen.

45. The process of claim 25, wherein the reaction products are acylated with a member selected from the group consisting of acetic acid anhydride, ketone, diketene, and mixtures thereof.

46. The process of claim 25, wherein the reaction products are cyanoethylated with acrylonitrile.

* * * * *